United States Patent
Zhang et al.

(10) Patent No.: US 10,556,930 B2
(45) Date of Patent: Feb. 11, 2020

(54) HOST CELLS AND METHODS FOR PRODUCING FATTY ACID-DERIVATIVES WITH HIGH BRANCHED-CHAIN PERCENTAGE

(71) Applicant: Washington University in St. Louis, St. Louis, MO (US)

(72) Inventors: Fuzhong Zhang, St. Louis, MO (US); Wen Jiang, St. Louis, MO (US); Gayle Bentley, St. Louis, MO (US)

(73) Assignee: Washington University, St. Louis, MO (US)

( * ) Notice: Subject to any disclaimer, the term of this patent is extended or adjusted under 35 U.S.C. 154(b) by 37 days.

(21) Appl. No.: 16/063,497

(22) PCT Filed: Dec. 16, 2016

(86) PCT No.: PCT/US2016/067324
§ 371 (c)(1),
(2) Date: Jun. 18, 2018

(87) PCT Pub. No.: WO2017/106747
PCT Pub. Date: Jun. 22, 2017

(65) Prior Publication Data
US 2018/0371031 A1  Dec. 27, 2018

Related U.S. Application Data

(60) Provisional application No. 62/268,191, filed on Dec. 16, 2015.

(51) Int. Cl.
| | | |
|---|---|---|
| *C07K 14/245* | (2006.01) | |
| *C12P 21/02* | (2006.01) | |
| *C12P 7/64* | (2006.01) | |
| *C12N 1/20* | (2006.01) | |
| *C12N 15/70* | (2006.01) | |

(52) U.S. Cl.
CPC .......... *C07K 14/245* (2013.01); *C12P 7/6409* (2013.01); *C12P 7/6436* (2013.01); *C12P 21/02* (2013.01); *C12N 1/20* (2013.01); *C12N 15/70* (2013.01); *C12Y 102/04004* (2013.01); *C12Y 203/01204* (2015.07); *C12Y 207/07063* (2013.01)

(58) Field of Classification Search
None
See application file for complete search history.

(56) References Cited

U.S. PATENT DOCUMENTS

| | | |
|---|---|---|
| 2003/0028915 A1 | 2/2003 | Tilton et al. |
| 2010/0081182 A1 | 4/2010 | Paul et al. |
| 2011/0244532 A1 | 10/2011 | Hu et al. |

OTHER PUBLICATIONS

Choi et al., β-Ketoacyl-Acyl Carver Protein Synthase III (FabH) Is a Deterining Factor in Branched-Chain Fatty Acid Biosynthesis; Journal Of Bacteriology, Jan. 2000, pp. 365-370.
Christensen et al., The Thermoplasma acidophilum LpIA-LpIB Complex Defines a new Class Of Bipartite Lipoate-protein Ligases; The Journal of Biological Chemistry, Aug. 7, 2009, vol. 284, No. 32, pp. 21317-21326.
Cicchillo et al., *Escherichia coli* Lipoyl Synthase Binds Two Distinct [4F3-4S] Clusters per Polypeptide; Biochemistry 2004, vol. 43, pp. 11770-11781.
Jiang et al., Enhanced Production of Branched-Chain Fatty Acids by Replacing 13-Ketoacyl-(acyl-carrier-protein) Synthase III (FabH); Biotechnology and Bioengineering, vol. 112, No. 8, pp. 1613-1622.
Lai et al., β-Ketoacyl-Acyl Carver Protein Synthase III (FabH) Is Essential for Bacterial Fatty Acid Synthesis; The Journal of Biological Chemistry; vol. 278, No. 51, Issue of Dec. 19, 2003, pp. 51494-51503.
Lee et al., Palladium-Catalyzed Inter- and Intramolecular Coupling Reactions of Aryl and Vinyl Halides Mediated by Indium, J. Biol. Eng., pp. 343-345.
Bun et al., Overproduction of a-Lipoic Acid by Gene Manipulated *Escherichia coli*; PLOS one; Jan. 9, 2017, 15 pages.
Ward et al., Branched-Chain a-Keto Acid Catabolism via the Gene Prodocts of the bkd Operon in Enterococcus faecalis: a New, Secreted Metabolite Serving as a Temporary Redox Sink; Journal of Bacteriology, Jun. 2000, pp. 3239-3246.

*Primary Examiner* — Kagnew H Gebreyesus
(74) *Attorney, Agent, or Firm* — Stinson LLP

(57) ABSTRACT

The present disclosure is generally related to transformed host cells and their use for the production of branched-chain acyl-ACPs, branched-chain acyl-ACP-derived chemicals and fuels, branched-chain fatty acids and producing branched-chain fatty acid-derived chemicals and fuels. More particularly, disclosed herein are transformed host cells and methods for producing branched-chain acyl-ACPs and branched-chain fatty acids in high titer and high percentages. Also disclosed are methods for producing specific branched-chain fatty acid species and producing branched-chain fatty acid-derived chemicals and fuels such as, for example, branched-chain alcohols and branched-chain fatty acid ethyl esters.

18 Claims, 16 Drawing Sheets

Specification includes a Sequence Listing.

HOST CELLS AND METHODS FOR PRODUCING FATTY ACID-DERIVATIVES WITH HIGH BRANCHED-CHAIN PERCENTAGE

CROSS-REFERENCE TO RELATED APPLICATIONS

This application claims priority to International Publication Number WO 2017/106747, filed on Dec. 16, 2016, which claims priority to U.S. Application Ser. No. 62/268, 191, filed on Dec. 16, 2015, the disclosures of which are hereby expressly incorporated by reference in their entireties.

STATEMENT REGARDING FEDERALLY SPONSORED RESEARCH OR DEVELOPMENT

This invention was made with government support under grant award number D13 AP00038 awarded by the Defense Advanced Research Projects Agency. The Government has certain rights in the invention.

INCORPORATION OF SEQUENCE LISTING

A paper copy of the Sequence Listing and a computer readable form of the Sequence Listing containing the file named "WUSTL_015503_ST25.txt", which is 15,328 bytes in size (as measured in MICROSOFT WINDOWS® EXPLORER), are provided herein and are herein incorporated by reference. This Sequence Listing consists of SEQ ID NO:1-11.

BACKGROUND OF THE DISCLOSURE

The present disclosure relates generally to transformed host cells and their use for the production of branched-chain acyl-acyl carrier proteins (acyl-ACP), producing branched-chain fatty acids, and producing branched-chain fatty acyl-ACP chemicals and fuels. More particularly, disclosed herein are transformed host cells and methods for producing branched-chain acyl-ACPs in high titer and high percentages. Also disclosed are methods for producing specific branched-chain fatty acid species and producing branched-chain fatty acid-derived chemicals and fuels such as, for example, branched-chain alcohols and branched-chain fatty acid ethyl esters.

Engineering microbes for the production of advanced biofuels with tunable physical and combustion properties is an attractive response to combat significant global petroleum supply concerns. Extensive research is currently focused on engineering the fatty acid biosynthetic pathway. Fatty acids are common precursors that can be readily converted to several types of chemicals including alkanes, alkenes, alcohols, aldehydes, and esters through either biological or chemical conversion. Bacteria utilize the multienzyme fatty acid synthase II (FASII) platform for fatty acid production, which has been extensively characterized and is widely conserved between organisms, making it an ideal engineering target for fatty acid-derived biofuels with tunable properties. A variety of strategies have been developed to increase titers and yields of fatty acid production in engineered microbes, including directing product formation via substrate supplementation, dynamic regulation of intermediate enzymes, thioesterase variation, and reversal of β-oxidation.

The majority of current efforts have focused on the production of straight-chain fatty acids and SCFA-derived chemicals. Meanwhile, branched chains improve vital fuel properties such as the freezing point, cold flow, and cloud point. Previous work demonstrated the capability to produce BCFA in *E. coli* through the expression of the branched-chain specific *B. subtilis* FabH2 in conjunction with BKD and the cytosolic *E. coli* thioesterase TesA. This, in addition to approaches such as dynamic regulation of FabH and control of product formation through branched-chain amino acids, resulted in production of 20% ante-iso BCFA. Knocking out the straight-chain-specific *E. coli* FabH and using a variety of branched-chain-specific FabH enzymes and upstream precursors increased the proportion of BCFA, ultimately generating 52% BCFA. Despite these systematic efforts, the predominant products in these studies were SCFAs, which have similar physico-chemical properties and are very difficult to separate from BCFAs. Accordingly, there exists a need for improved methods for BCFA production.

BRIEF DESCRIPTION OF THE DISCLOSURE

The present disclosure relates generally transformed host cells and their use for the production of branched-chain fatty acyl-ACP and producing branched-chain fatty acyl-ACP chemicals and fuels. More particularly, the present disclosure is directed to transformed host cells and methods for producing branched-chain fatty acyl-ACPs in high titer and high percentages. Also disclosed are methods for producing specific branched-chain fatty acid species and producing branched-chain fatty acid-derived chemicals and fuels such as, for example, branched-chain alcohols and branched-chain fatty acid ethyl esters.

In one aspect, the present disclosure is directed to a transformed host cell for producing branched-chain acyl-acyl carrier protein (acyl-ACP). The transformed host cell comprises a nucleic acid comprising a sequence encoding a branched-chain α-keto acid dehydrogenase; a nucleic acid comprising a sequence encoding a β-ketoacyl-[acyl-carrier-protein] synthase III; and a nucleic acid comprising a sequence encoding a lipoyl ligase.

In one aspect, the present disclosure is directed to a transformed host cell for producing branched-chain fatty acid. The transformed host cell comprises a nucleic acid encoding a lipoyl ligase; a nucleic acid encoding an octanoyltransferase; wherein at least one of the nucleic acids is operably linked to a nucleic acid encoding an iron sulfur cluster chaperone.

In one aspect, the present disclosure is directed to a transformed host cell for producing branched-chain fatty acid. The transformed host cell comprises a nucleic acid encoding a lipoate synthase; a nucleic acid encoding an octanoyltransferase; wherein at least one of the nucleic acids is operably linked to a nucleic acid encoding an iron sulfur cluster chaperone.

In one aspect, the present disclosure is directed to a method for producing a branched-chain fatty acyl-acyl carrier protein. The method includes providing a transformed host cell comprising a nucleic acid encoding a branched-chain α-keto acid dehydrogenase; a nucleic acid encoding a β-ketoacyl-[acyl-carrier-protein] synthase III; a nucleic acid encoding a lipoyl ligase A; and wherein at least one of the nucleic acids is operably linked to a nucleic acid encoding an iron sulfur cluster chaperone; and culturing the transformed host cell in a culture medium comprising lipoic acid under conditions permitting the transformed host cell to produce a branched-chain acyl-ACP.

In one aspect, the present disclosure is directed to a method for producing a branched-chain acyl-acyl carrier protein. The method includes providing a transformed host cell comprising a nucleic acid encoding a branched-chain α-keto acid dehydrogenase; a nucleic acid encoding a β-ketoacyl-[acyl-carrier-protein] synthase III; and a nucleic acid comprising a sequence encoding a lipoate synthetase; and a nucleic acid encoding an octanoyltransferase; and culturing the transformed host cell in a culture medium under conditions permitting the transformed host cell to produce a branched-chain acyl-ACP.

In one aspect, the present disclosure is directed to a transformed host cell for producing branched-chain fatty acids. The transformed host cell comprises a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an Acyl-CoA thioesterase I; and a nucleic acid comprising a sequence encoding a lipoyl ligase A.

In another aspect, the present disclosure is directed to a method for producing specific branched-chain fatty acid species. The method comprises: providing a transformed host cell comprising a nucleic acid comprising a sequence encoding a branched-chain α-keto acid dehydrogenase; a nucleic acid comprising a sequence encoding a branched-chain-specific β-ketoacyl-[acyl-carrier-protein] synthase III; and a nucleic acid encoding a lipoyl ligase A; and culturing the transformed host cell in a culture medium comprising lipoic acid and an α-keto acid, wherein the transformed host cell produces a specific branched-chain fatty acid species.

In another aspect, the present disclosure is directed to a transformed host cell comprising a nucleic acid comprising a branched-chain α-keto acid dehydrogenase; a nucleic acid encoding a branched-chain-specific β-ketoacyl-[acyl-carrier-protein] synthase III; a nucleic acid encoding an acyl-CoA thioesterase I; a nucleic acid encoding an octanoyltransferase (lipB); and a nucleic acid encoding a lipoyl synthase (lipA).

In another aspect, the present disclosure is directed to a method for producing a branched-chain fatty acid species. The method comprises: providing a host cell comprising a nucleic acid encoding a branched-chain α-keto acid dehydrogenase; a nucleic acid encoding a branched-chain-specific β-ketoacyl-[acyl-carrier-protein] synthase III; a nucleic acid encoding an octanoyltransferase (lipB); and a nucleic acid encoding a lipoyl synthase (lipA); and culturing the transformed host cell in a culture medium under conditions permitting the transformed host cell to produce a branched-chain acyl-ACP.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 2A depicts the growth of fatty acid-overproducing strains with (SC03) or without (SC01) BKD overexpression (p<0.01, Student's T-test). FIG. 2B depicts the overexpression of BKD reduction of free fatty acid (FFA) production (p<0.01).

FIG. 3A depicts a model illustrating the proposed mechanism of BKD toxicity. (i) Native 2-oxoacid dehydrogenases (OADHs, blue) are lipoylated for proper function. (ii) When BKD (yellow) is overexpressed, protein lipoylation capability is depleted, leading to unlipoylated OADHs. (iii) OADHs can be fully lipoylated through the overexpression of LplA, which ligates lipoic acid to the E2 subunit of each OADH. FIG. 3B depicts a 12% SDS-PAGE gel stained with Coomassie blue (top) and corresponding Western Blot (bottom) of the same samples blotted using an anti-lipoyl monoclonal antibody. When BKD was expressed, lipoylation of pyruvate dehydrogenase was reduced. Overexpression of LplA together with lipoic acid supplementation restored PDH lipoylation and increased lipoylation of ODH and BKD.

FIG. 4A depicts the total FFAs and BCFAs produced by $_{Bs}$FabH-containing strains BC11A and BC11L. Supplementation of lipoic acid to BC11L dramatically enhanced BCFA production. FIG. 4B depicts the FFA profiles produced by each strain in (FIG. 4A). Numbers on the x-axis indicate carbon number of each FA species. FIG. 4C depicts the total FFAs and BCFAs produced by $_{Sa}$FabH-containing strains BC13A and BC13L. FIG. 4D depicts the FFA profiles produced by each strain in FIG. 4C.

FIG. 5A depicts the series of strains with different combinations of bkd integration, FadR, and LplA expression. BCFA titer of each strain is shown with filled columns. BCFA percentage is shown by open squares FIG. 5B depicts the FFA profile of strains BC33A, BC33L, and BC33FL.

FIG. 6A depicts the FFA profiles of the strain under each cultivation condition are shown. FIG. 6B depicts the percent of BCFAs corresponding to each branch position.

FIG. 7A depicts the distribution of membrane FA species in BC13A, BC13L, and WT *E. coli*. The residue amount of BCFAs in BC13A and BC13L (<5%) were likely due to unextracted free BCFAs because the FFA extraction efficiency of the employed method is ~90% (data not shown). FIG. 7B depicts the proportion of BCFA in FFA and membrane lipid of each analyzed strain. * BCFA percentage of WT *E. coli* was assumed to be zero based on the detection limit of GC-MS and the canonical *E. coli* FA composition.

FIG. 8A depicts a graphical illustration of pathways for FAs to either undergo membrane incorporation or to be utilized as a carbon source through β-oxidation. Green arrows indicated allowed pathway. Red, dashed arrows may be restricted to BCFA in *E. coli*. FIG. 8B depicts WT *E. coli* (MG1655) or DH1 AfadE were grown on either 1 mg/mL of 14-methyl-pentadecanoic acid (isopalmitic acid, C15 iso), 1 mg/mL of palmitic acid (C16), or 2% glucose in minimal medium. Strains MG1655 grew on isopalmitic acid with a slower rate than that in palmitic acid or glucose. As a negative control, strain DH1 AfadE showed no growth on isopalmitic acid.

FIG. 9A depicts that supplementation of strain BC11A with lipoic acid did not increase BCFA. In the absence of arabinose, the inducer for LplA expression, strain BC11L produced a similar amount of BCFAs to that with arabinose, indicating that leaking expression of LplA from PBAD was sufficient for protein lipoylation. FIG. 9B depicts the FFA profiles of various strains.

FIG. 10A depicts the total FFAs and BCFAs produced by strains BC11A, BC31A and BC31F. Expression of FadR enhanced both total FFA and BCFA production. FIG. 10B depicts the FFA profiles produced by each strain in FIG. 10A. FadR overexpression primarily increased unsaturated FAs.

FIG. 12A depicts the exogenous and endogenous lipoylation pathways in *E. coli*. * indicates a secondary activity of LipB. FIG. 12B depicts the BCFA production from strains carrying an endogenous lipoylation pathway compared with that carrying an exogenous lipoylation pathway. Relative BCFA titers shown for each modification are noted below each column in FIG. 12B. Synthetic RBS denotes control of lipA-lipB each under strong, synthetic RBSs.

DETAILED DESCRIPTION

Figure 1:
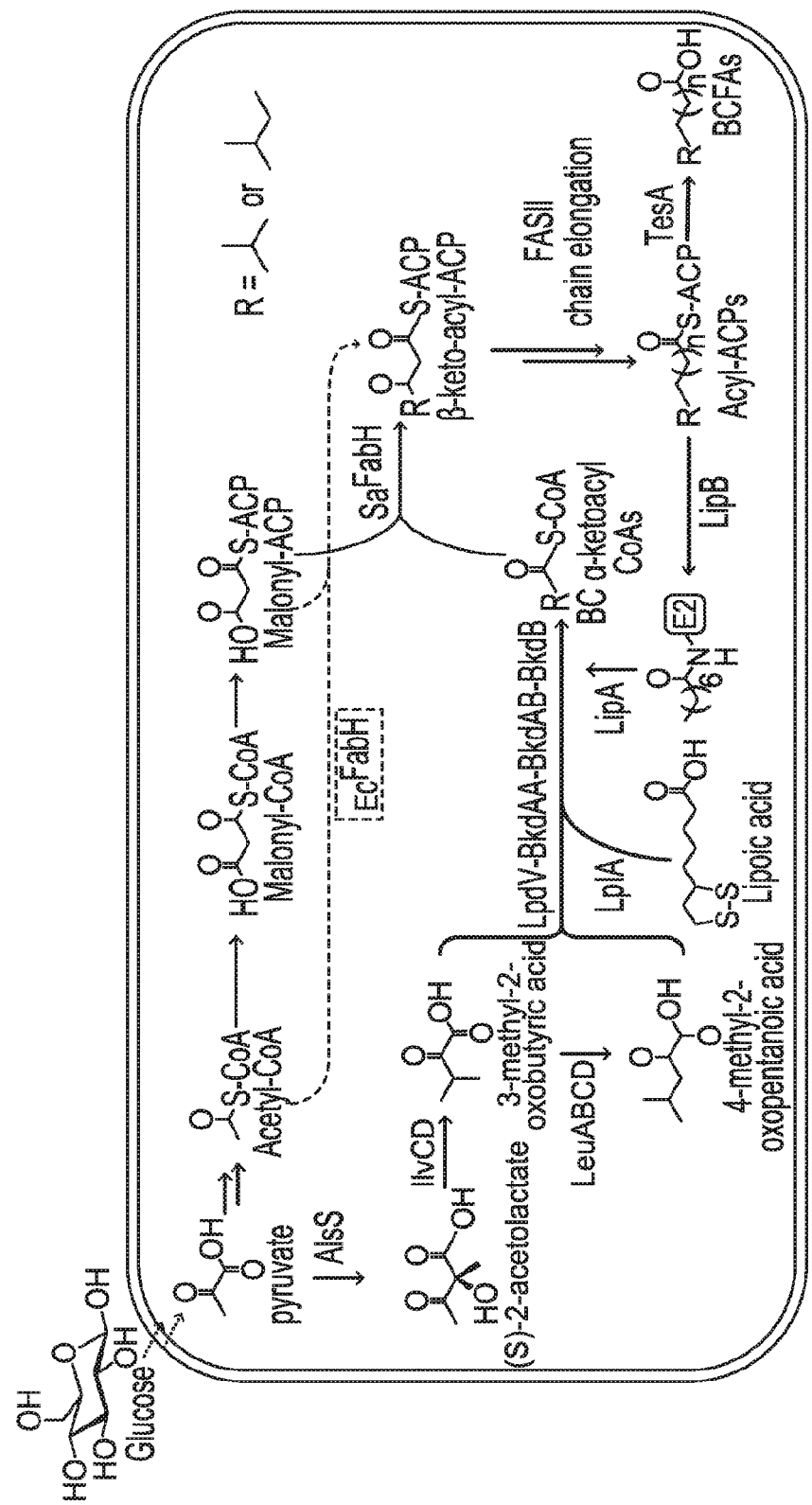
FIG. 1 depicts the biosynthetic pathway for the production of high percentage branched-chain fatty acids (BCFAs) in *E. coli* as described herein. BCFAs were produced by expression of a *B. subtilis* branched-chain α-ketoacid dehydrogenase complex (LpdV, BkdAA, BkdAB, and BkdB), a branched-chain α-ketoacyl-CoA-specific FabH (e.g. $_{Sa}$FabH) and a cytosolic thioesterase (e.g., TesA). Cellular branched-chain α-ketoacid precursors can be enriched by engineering a branched-chain amino acid biosynthesis pathway (e.g., AlsS, IlvCD, and LeuABCD). The percentage of BCFA products can be dramatically enhanced by engineering protein lipoylation, either through an endogenous pathway (overexpression of LipB and LipA) or an exogenous pathway (LplA overexpression in combination with lipoic acid supplement). *E. coli* native patways are colored gray. Overexpression enzymes are colored orange. Native $_{Ec}$FABH (boxed with dotted line) was deleted from the engineered strain

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed are host cells and methods for producing branched-chain fatty acids in high titer and high percentages. Also disclosed are methods for producing specific branched-chain fatty acid species and producing branched-chain fatty acid-derived chemicals and fuels such as, for example, branched-chain alcohols and branched-chain fatty acid ethyl esters.

As used herein, "expression vector" refers to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

As used herein, "overexpressed" and "overexpression" refer to the artificial expression of a gene in increased quantity as compared to the expression of the native (endogenous) gene.

The term "transformed host cell" is used according to its ordinary meaning as understood by those skilled in the art to refer to a genetically altered cell resulting from the uptake or insertion of and incorporation of exogenous genetic material. Transformation can occur in which exogenous genetic material passes from one host cell (e.g., bacterium) to another, by conjugation (transfer of genetic material between two bacterial cells in direct contact) and by transduction (injection of foreign DNA by a bacteriophage virus into the host cell).

Percent identity over a determined length can be determined by using methods known to those skilled in the art. The terms "identical" or percent "sequence identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms or by manual alignment and visual inspection.

In one aspect, the present disclosure is directed to a transformed host cell for producing branched-chain acyl-acyl carrier protein (acyl-ACP). The transformed host cell comprises a nucleic acid comprising a sequence encoding a branched-chain α-keto acid dehydrogenase; a nucleic acid comprising a sequence encoding a β-ketoacyl-[acyl-carrier-protein] synthase III; and a nucleic acid comprising a sequence encoding a lipoyl ligase. At least one of the nucleic acid comprising a sequence encoding a branched-chain α-keto acid dehydrogenase; the nucleic acid comprising a sequence encoding a β-ketoacyl-[acyl-carrier-protein] synthase III; and the nucleic acid comprising a sequence encoding a lipoyl ligase A are overexpressed.

A particularly suitable lipoyl ligase is lipoyl ligase A (also referred to as lipoate-protein ligase A (EC:6.3.1.20)), which is encoded by the lplA gene (GeneID 944865). Other suitable lipoyl ligase A include those having 75%, 80%, 85%, 90%, 91%, 92%, 93%, 94%, 95%, 96%, 97%, 98%, 99%, or higher amino acid sequence identity to the amino acid sequence encoded by GeneID 944865. Lipoyl ligase A catalyzes both the ATP-dependent activation of exogenously supplied lipoate to lipoyl-AMP and the transfer of the activated lipoyl onto the lipoyl domains of lipoate-dependent enzymes. Is also able to catalyze very poorly the transfer of lipoyl and octanoyl moiety from their acyl carrier protein In one embodiment, the transformed host cell further includes a nucleic acid encoding an acyl-CoA thioesterase I.

In another aspect the transformed host cell further includes a nucleic acid encoding FadR.

In another aspect at least one of the nucleic acids can be operably linked to a nucleic acid encoding an iron sulfur cluster chaperone. Iron sulfur cluster chaperones participate in electron transfer, substrate binding/activation, iron/sulfur storage, regulation of gene expression, and enzyme activity.

A particularly suitable iron sulfur cluster chaperone is the isc operon that is encoded by iscS, iscU, iscA, hscB, hscA, fdx, iscX.

In one aspect, the present disclosure is directed to a transformed host cell for producing branched-chain fatty acid. The transformed host cell comprises a nucleic acid encoding a lipoyl ligase; a nucleic acid encoding an octanoyltransferase; wherein at least one of the nucleic acids is operably linked to a nucleic acid encoding an iron sulfur cluster chaperone.

A particularly suitable lipoyl ligase is lipoyl ligase A as described herein.

A particularly suitable iron sulfur cluster chaperone is the isc operon as described herein.

A particularly suitable octanoyltransferase is encoded by the lipB gene (for example, GeneID 945217). Other suitable octanoyltransferases include those having 75%, 80%, 85%, 90%, 91%, 92%, 93%, 94%, 95%, 96%, 97%, 98%, 99%, or higher amino acid sequence identity to the amino acid sequence encoded by GeneID 945217. LipB catalyzes the transfer of endogenously produced octanoic acid from octanoyl-acyl-carrier-protein onto the lipoyl domains of lipoate-dependent enzymes. Lipoyl-ACP can also act as a substrate.

In one embodiment, the transformed host cell further includes a nucleic acid encoding an acyl-CoA thioesterase I as described herein.

In another aspect the transformed host cell further includes a nucleic acid encoding FadR as described herein.

In one aspect, the present disclosure is directed to a transformed host cell for producing branched-chain fatty acid. The transformed host cell comprises a nucleic acid encoding a lipoate synthase; a nucleic acid encoding an octanoyltransferase; wherein at least one of the nucleic acids is operably linked to a nucleic acid encoding an iron sulfur cluster chaperone.

A particularly suitable lipoate synthase (also referred to as lipoyl synthase) encoded by the lipA gene (GeneID 945227). Other suitable octanoyltransferases include those having 75%, 80%, 85%, 90%, 91%, 92%, 93%, 94%, 95%, 96%, 97%, 98%, 99%, or higher amino acid sequence identity to the amino acid sequence encoded by GeneID 945227. Lipoate synthase catalyzes the radical-mediated insertion of two sulfur atoms into the C-6 and C-8 positions of the octanoyl moiety bound to the lipoyl domains of lipoate-dependent enzymes, thereby converting the octanoylated domains into lipoylated derivatives.

A particularly suitable octanoyltransferase is encoded by the lipB gene as described herein.

A particularly suitable iron sulfur cluster chaperone is the isc operon as described herein.

In one aspect, the present disclosure is directed to a method for producing a branched-chain fatty acyl-acyl carrier protein. The method includes providing a transformed host cell comprising a nucleic acid encoding a branched-chain α-keto acid dehydrogenase; a nucleic acid encoding a β-ketoacyl-[acyl-carrier-protein] synthase III; a nucleic acid encoding a lipoyl ligase A; and wherein at least one of the nucleic acids is operably linked to a nucleic acid encoding an iron sulfur cluster chaperone; and culturing the transformed host cell in a culture medium comprising lipoic acid under conditions permitting the transformed host cell to produce a branched-chain acyl-ACP.

Suitable transformed host cells are described herein.

In one aspect, the present disclosure is directed to a method for producing a branched-chain acyl-acyl carrier protein. The method includes providing a transformed host cell comprising a nucleic acid encoding a branched-chain α-keto acid dehydrogenase; a nucleic acid encoding a β-ketoacyl-[acyl-carrier-protein] synthase III; and a nucleic acid comprising a sequence encoding a lipoate synthetase; and a nucleic acid encoding an octanoyltransferase; and culturing the transformed host cell in a culture medium under conditions permitting the transformed host cell to produce a branched-chain acyl-ACP.

Suitable transformed host cells are described herein.

In one aspect, the present disclosure is directed to a transformed host cell for producing branched-chain fatty acids. The transformed host cell comprises a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an Acyl-CoA thioesterase I; and a nucleic acid comprising a sequence encoding a lipoyl ligase A.

Suitable transformed host cells are described herein.

In another aspect, the present disclosure is directed to a method for producing specific branched-chain fatty acid species. The method comprises: providing a transformed host cell comprising a nucleic acid comprising a sequence encoding a branched-chain α-keto acid dehydrogenase; a nucleic acid comprising a sequence encoding a branched-chain-specific β-ketoacyl-[acyl-carrier-protein] synthase III; and a nucleic acid encoding a lipoyl ligase A; and culturing the transformed host cell in a culture medium comprising lipoic acid and an α-keto acid, wherein the transformed host cell produces a specific branched-chain fatty acid species.

Suitable transformed host cells are described herein.

In another aspect, the present disclosure is directed to a transformed host cell comprising a nucleic acid comprising a branched-chain α-keto acid dehydrogenase; a nucleic acid encoding a branched-chain-specific β-ketoacyl-[acyl-carrier-protein] synthase III; a nucleic acid encoding an acyl-CoA thioesterase I; a nucleic acid encoding an octanoyltransferase (lipB); and a nucleic acid encoding a lipoyl synthase (lipA).

Suitable transformed host cells are described herein.

In another aspect, the present disclosure is directed to a method for producing a branched-chain fatty acid species. The method comprises: providing a host cell comprising a nucleic acid encoding a branched-chain α-keto acid dehydrogenase; a nucleic acid encoding a branched-chain-specific β-ketoacyl-[acyl-carrier-protein] synthase III; a nucleic acid encoding an octanoyltransferase (lipB); and a nucleic acid encoding a lipoyl synthase (lipA); and culturing the transformed host cell in a culture medium under conditions permitting the transformed host cell to produce a branched-chain acyl-ACP.

Suitable transformed host cells are described herein.

In one aspect, the present disclosure is directed to a transformed host cell for producing branched-chain fatty acids. The transformed host cell includes a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an acyl-CoA thioesterase I; and a nucleic acid comprising a sequence encoding a lipoyl ligase A. In another embodiment, the transformed host cell can further include a nucleic acid comprising a sequence encoding an acyl-CoA/ACP reductase (maqu2220 from *Marinobacter aquaeolei* Gene ID 4657301 or AAR, encoded by aar *Synechococcus elongatus* Gene ID: 3775018) for producing an alcohol. In another embodiment, the transformed host cell can further include a nucleic acid comprising a sequence encoding an acyl-ACP reductase (AAR, encoded by aar *Synechococcus elongatus* Gene ID: 3775018aao) and aldehyde deformylating oxygenase (ADO, encoded by ado, *Prochlorococcus marinus*) for producing an alkane. In another embodiment, the transformed host cell can further include a nucleic acid comprising a sequence encoding a wax ester synthase (encoded by adp1, *Acinetobacter calcoaceticus*, Gene ID: 25683077) for producing a fatty acid ethyl ester.

In one embodiment, the nucleic acid encoding the branched-chain α-keto acid dehydrogenase can be obtained from an organism selected from *Bacillus subtilis* and *Staphylococcus aureus*. In another embodiment, the nucleic acid encoding a branched-chain α-keto acid dehydrogenase has about 80%, about 85%, about 90%, about 95%, about 96%, about 97%, about 98%, and about 99% sequence identity to SEQ ID NO:1 (bkdAA Gene ID:14770064), SEQ ID NO:2 (bkdAB Gene ID:14770063), SEQ ID NO:3 (bkdB Gene ID:14770062) and SEQ ID NO:4 (lpdV Gene ID:14770065). Branched-chain α-keto acid dehydrogenase (encoded by bkd) is a 2-oxodehydrogenase that catalyzes the conversion of branched-chain α-keto acids to branched-chain-CoA starters (BCCSs), which serve as the substrate of a BCCS-specific FabH, generating branched-chain acyl-ACPs which undergo elongation in the fatty acid synthase II (FASII) complex. As known to those skilled in the art, sequences obtained from one organism can be codon optimized for expression in a different microorganism. Codon optimization can be performed using a commercially available computer programs (e.g., GeneScript USA Inc., Piscataway, N.J.; EnCor Biotechnology Inc., Gainesville, Fla.; Integrated DNA Technologies, Coralville, Iowa).

In one embodiment, the nucleic acid comprises a sequence encoding a branched-chain-specific β-ketoacyl-[acyl-carrier-protein] synthase III. In particular, the branched-chain-specific β-ketoacyl-[acyl-carrier-protein] synthase III is the only β-ketoacyl-[acyl-carrier-protein] synthase III. In particular, the straight-chain-specific FabH is deleted in the transformed host cell and functionally replaced with one of the branched-chain-specific FabHs. For example, the native fabH gene can be deleted and functionally replaced with a β-Ketoacyl-(acyl-carrier-protein) synthase III enzyme with high branched-chain acyl-CoA specificity. β-ketoacyl-[acyl-carrier-protein] synthase III (EC: 2.3.1.180) catalyzes the condensation reaction of fatty acid synthesis by the addition to an acyl acceptor of two carbons from malonyl-ACP. β-ketoacyl-[acyl-carrier-protein] synthase III catalyzes the first condensation reaction which initiates fatty acid synthesis and may therefore play a role in governing the total rate of fatty acid production. β-ketoacyl-[acyl-carrier-protein] synthase III possesses both acetoacetyl-ACP synthase and acetyl transacylase activities and has some substrate specificity for acetyl-CoA. Its substrate specificity determines the biosynthesis of straight-chain of fatty acids instead of branched-chain. 3-oxoacyl-[acyl-carrier-protein] synthase 3 is encoded by the fabH gene in *E. coli*. (Gene ID:946003). Particularly suitable branched-chain-specific β-ketoacyl-(acyl-carrier-protein) synthase IIIs can be selected from *Staphylococcus aureus* FabH ($_{Sa}$FabH) and *Bacillus subtilis* FabH2 ($_{Bs}$FabH2); $_{Bs}$FabH1; and a *Listeria monocytogenes* FabH. In another embodiment, the nucleic acid encoding a $_{Sa}$FabH has about 80%, about 85%, about 90%, about 95%, about 96%, about 97%, about 98%, and about 99% sequence identity to SEQ ID NO:5 (*Staphylococcus aureus* Gene ID:23196764). In another embodiment, the nucleic acid encoding a $_{Bs}$FabH has about 80%, about 85%, about 90%, about 95%, about 96%, about 97%, about 98%, and about 99% sequence identity to SEQ ID NO:6 (*Bacillus subtilis* Gene ID:939306). β-Ketoacyl-(acyl-carrier-protein) Synthase III (EC 2.3.1.180) is an enzyme that initiates both straight- and branched-chain fatty-acid biosynthesis, with the substrate specificity in an organism reflecting the fatty-acid composition found in that organism. Codon optimization can be performed using a commercially available computer programs as described herein.

In one embodiment, the nucleic acid encoding an acyl-CoA thioesterase I (EC 3.1.1.5) has about 80%, about 85%, about 90%, about 95%, about 96%, about 97%, about 98%, and about 99% sequence identity to SEQ ID NO:7 (Gene ID: 945127). Codon optimization can be performed using a commercially available computer programs as described herein.

In one embodiment, the nucleic acid encoding a lipoyl ligase A has about 80%, about 85%, about 90%, about 95%, about 96%, about 97%, about 98%, and about 99% sequence identity to SEQ ID NO:8 (Gene ID:944865). Lipoyl ligase A (EC 2.7.7.63) is an enzyme that catalyzes the transfer of the lipoyl group from lipoyl-AMP to the specific lysine residue of lipoyl domains of lipoate-dependent enzymes. Codon optimization can be performed using a commercially available computer programs as described herein.

The transformed host cell can further include a nucleic acid encoding a FadR (fatty acid degradation R; fatty acid metabolism regulon transcriptional regulator). In one embodiment, the nucleic acid encoding FadR has about 80%, about 85%, about 90%, about 95%, about 96%, about 97%, about 98%, and about 99% sequence identity to SEQ ID NO:9 (*E. coli* Gene ID:948652). FadR negatively regulates expression of the fatty acid degradation (fad) genes at the transcriptional level and positively regulates expression of fatty acid biosynthesis genes. Codon optimization can be performed using a commercially available computer programs as described herein.

In another aspect, the present disclosure is directed to a transformed host cell for producing branched-chain fatty acids. The transformed host cell includes a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an acyl-CoA thioesterase I; a nucleic acid comprising a sequence encoding a lipoyl (octanoyl) synthase (lipB); and a nucleic acid comprising a sequence encoding a lipoyl synthase (ZiM). Suitable branched-chain α-keto acid dehydrogenases; β-ketoacyl-[acyl-carrier-protein] synthase IIIs; and Acyl-CoA thioesterase are described herein. A suitable lipB gene can be, for example, *E. coli* Gene ID:945217. In one embodiment, the nucleic acid encoding lipB has about 80%, about 85%, about 90%, about 95%, about 96%, about 97%, about 98%, and about 99% sequence identity to SEQ ID NO:10 (*E. coli* Gene ID:945217). A suitable lipA gene can be, for example *E. coli* Gene ID:945227. In one embodiment, the nucleic acid encoding lipA has about 80%, about 85%, about 90%, about 95%, about 96%, about 97%, about 98%, and about 99% sequence identity to SEQ ID NO:11 (*E. coli* Gene ID:945227). Endogenous lipoylation begins when lipB transfers an octanoyl moiety from the acyl carrier protein to a 2-oxoacid dehydrogenase E2 subunit. lipA then closes the ring by inserting sulfur to positions 6 and 8, resulting in a fully lipoylated E2 subunit. During normal cell growth, lipB and lipA catalyze lipoylation of native dehydrogenases. When additional 2-oxoacid dehydrogenases are overexpressed, such as BKD, lipoylation is reduced. Upregulating lipB and lipA can restore lipoylation by increased ligation of octanoyl-ACP to the E2 subunit and sulfur insertion. In another embodiment, the transformed host cell can further include a nucleic acid comprising a sequence encoding an acyl-CoA/ACP reductase (maqu2220 from *Marinobacter aquaeolei* Gene ID 4657301 or AAR, encoded by aar *Synechococcus elongatus* Gene ID: 3775018) for producing an alcohol. In another embodiment, the transformed host cell can further include a nucleic acid comprising a sequence encoding an acyl-ACP reductase (AAR, encoded by aar *Synechococcus elongatus* Gene ID: 3775018aao) and aldehyde deformylating oxygenase (ADO, encoded by ado, *Prochlorococcus marinus*) for producing an alkane. In another embodiment, the transformed host cell can further include a nucleic acid comprising a sequence encoding a wax ester synthase (encoded by adp1, *Acinetobacter calcoaceticus*, Gene ID: 25683077) for producing a fatty acid ethyl ester.

Any microbial cell can be used as the host cell to be transformed with the exogenous nucleic acids encoding the proteins described herein. Suitable microbial cells include, for example, *Escherichia, Acinetobacter, Azotobacter, Bacillus, Bradyrizobium, Caulobacter, Chlamydia, Clostridium, Enterococcus, Klebsiella, Myxococcus, Planctomyces, Pseudomonas, Rhizobium, Rhodobacter, Salmonella, Sinorhizobium, Streptomyces, Rhodotorula, Lactococcus, Saccharomyces, Aspergillus, Yarrowia, Arabidopsis, Arachis, Vitis, Gossypium, Vibrio*, and cyanobacteria. Particularly suitable host cells can be *Escherichia coli*.

A particularly suitable transformed *E. coli* host cell is one that overexpresses BKD in combination with TesA and a branch-chain-specific FabH, in which strain fabH is deleted from the parental *E. coli* MG1655 background (see, Lai and Cronan, J. Biol. Chem. Dec. 19, 2003; 278(51):51494-503, which is incorporated by reference).

In another aspect, the present disclosure is directed to methods for producing branched-chain fatty acids in high percentages. In one embodiment, the method includes providing a transformed host cell comprising a nucleic acid encoding a branched-chain α-keto acid dehydrogenase; a nucleic acid encoding a branched-chain-specific β-Ketoacyl-(acyl-carrier-protein) Synthase III; a nucleic acid comprising a sequence encoding an acyl-CoA thioesterase I; and a nucleic acid encoding a lipoyl ligase A; and culturing the transformed host cell in a culture medium comprising lipoic acid, wherein the transformed host cell produces a branched-chain fatty acid. In particular, the branched-chain-specific β-ketoacyl-[acyl-carrier-protein] synthase III is the only β-ketoacyl-[acyl-carrier-protein] synthase III. In particular, the straight-chain-specific FabH is deleted in the transformed host cell and functionally replaced with one of the branched-chain-specific FabHs. For example, the native fabH gene can be deleted and functionally replaced with a β-Ketoacyl-(acyl-carrier-protein) synthase III enzyme with high branched-chain acyl-CoA specificity. In another embodiment, the method includes providing a transformed host cell comprising a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an Acyl-CoA thioesterase I; a nucleic acid comprising a sequence encoding a lipoyl (octanoyl) synthase (lipB); and a nucleic acid comprising a sequence encoding a lipoyl synthase (lipA); and culturing the transformed host cell in a culture medium, wherein the transformed host cell produces a specific branched-chain fatty acid species. In particular, the branched-chain-specific β-ketoacyl-[acyl-carrier-protein] synthase III is the only β-ketoacyl-[acyl-carrier-protein] synthase III. In particular, the native fabH gene can be deleted and functionally replaced with a 3-Ketoacyl-(acyl-carrier-protein) synthase III enzyme with high branched-chain acyl-CoA specificity.

The method can produce branched-chain fatty acids at a percentage of greater than 80% of the total fatty acids produced. The level of branched-chain fatty acids produced can be increased by about 4-fold as compared to a host cell cultured in a culture medium lacking lipoic acid. In another embodiment, the level of branched-chain fatty acids produced can be increased by about 4-fold as compared to a host cell lacking a nucleic acid comprising a sequence encoding LipB; and a nucleic acid comprising a sequence encoding LipA.

In one embodiment, the branched-chain fatty acid produced includes an odd-chain-iso branched-chain fatty acid. The odd-chain-iso branched-chain fatty acid is selected from 7-methyl-octanoic acid (C9 iso), 9-methyl-decanoic acid (C11 iso), 11-methyl-dodecanoic aid (C13 iso), 13-methyl-tetradecanoic acid (C15 iso), 15-methyl-hexadecanoic acid (C17 iso) and combinations thereof. In another embodiment, the branched-chain fatty acid produced includes an even-chain-iso branched-chain fatty acid. The even-chain-iso branched-chain fatty acid is selected from 10-methyl-undecanoic acid (C12 iso), 12-methyl-tridecanoic acid (C14 iso), 14-methyl-pentadecanoic acid (C16 iso), 16-methyl-heptadecanoic acid (C18 iso) and combinations thereof. Further, the branched-chain fatty acid produced can generate an odd-chain ante-iso branched-chain fatty acid. The odd-chain ante-iso branched-chain fatty acid is selected from 6-methyl-octanoic acid (C9 anteiso), 8-methyl-decanoic acid (C11 anteiso), 10-methyl-dodeanoic acid (C13 anteiso), 12-methyl-tetradecanoic acid (C15 anteiso), 14-methyl-hexadecanoic acid (C17 anteiso), and combinations thereof.

The nucleic acid encoding the branched-chain α-keto acid dehydrogenase can be obtained from any organism having the branched-chain α-keto acid dehydrogenase, as described herein. In one embodiment, the nucleic acid encoding the branched-chain α-keto acid dehydrogenase can be obtained from *Bacillus subtilis* and *Staphylococcus aureus*, as described herein. In another embodiment, the nucleic acid encoding a branched-chain α-keto acid dehydrogenase has about 80%, about 85%, about 90%, about 95%, about 96%, about 97%, about 98%, and about 99% sequence identity to SEQ ID NO:1 (bkdAA Gene ID: 14770064), SEQ ID NO:2 (bkdAB Gene ID: 14770063), SEQ ID NO:3 (bkdB Gene ID:14770062) and SEQ ID NO:4 (lpdV Gene ID:14770065), as described herein.

In one embodiment, the nucleic acid encoding a lipoyl ligase A has about 80%, about 85%, about 90%, about 95%, about 96%, about 97%, about 98%, and about 99% sequence identity to SEQ ID NO:8 (Gene ID:944865) Lipoyl ligase A (EC 2.7.7.63), as described herein.

The transformed host cell further includes a nucleic acid encoding a β-Ketoacyl-(acyl-carrier-protein) Synthase III, as described herein. Particularly suitable β-Ketoacyl-(acyl-carrier-protein) synthase IIIs can be selected from $_{Sa}$FabH and $_{Bs}$FabH2, as described herein. In another embodiment, the nucleic acid encoding a $_{Sa}$FabH has about 80%, about 85%, about 90%, about 95%, about 96%, about 97%, about 98%, and about 99% sequence identity to SEQ ID NO:5 (*Staphylococcus aureus* Gene ID:23196764). In another embodiment, the nucleic acid encoding a $_{Bs}$FabH has about 80%, about 85%, about 90%, about 95%, about 96%, about 97%, about 98%, and about 99% sequence identity to SEQ ID NO:6 (*Bacillus subtilis* Gene ID:939306), as described herein. The branched-chain-specific β-ketoacyl-[acyl-carrier-protein] synthase III is the only β-ketoacyl-[acyl-carrier-protein] synthase III. In particular, the straight-chain-specific FabH is deleted in the transformed host cell and functionally replaced with one of the branched-chain-specific FabHs. For example, the native fabH gene can be deleted and functionally replaced with a β-Ketoacyl-(acyl-carrier-protein) synthase III enzyme with high branched-chain acyl-CoA specificity.

The transformed host cell can further include a nucleic acid encoding a FadR (fatty acid degradation R), as described herein. In one embodiment, the nucleic acid encoding FadR has about 80%, about 85%, about 90%, about 95%, about 96%, about 97%, about 98%, and about 99% sequence identity to SEQ ID NO:9 (*E. coli* Gene ID:948652), as described herein.

Any microbial cell can be used as the host cell as described herein. Particularly suitable host cells can be *Escherichia coli*.

A particularly suitable transformed *E. coli* host cell is one that overexpresses BKD in combination with TesA and a branch-chain-specific FabH, in which strain fabH is deleted from the parental *E. coli* MG1655 background (see, Lai and Cronan, J. Biol. Chem. Dec. 19, 2003; 278(51):51494-503, which is incorporated by reference).

For branched-chain fatty acid production, cells are pre-cultivated in LB medium with relevant antibiotics (for example, kanamycin, ampicillin, and chloramphenicol). Overnight cultures can then be used to inoculate a minimal medium such as modified M9 minimal medium with corresponding antibiotics for adaptation. Overnight cultures from the minimal medium can then be used to inoculate the same fresh minimal medium and induced with relevant inducers (e.g., Isopropyl β-D-1-thiogalactopyranoside (IPTG), arabinose) after reaching the desired OD$_{600}$ (e.g., OD$_{600}$ of 0.8-1.0). For α-keto acids supplementation, one of the α-keto acids β-methyl-2-oxobutyric acid, 4-methyl-2-oxopentanoic acid, or 3-methyl-2-oxopentanoic acid) is supplemented in the minimal medium (e.g., a suitable amount is 1 g/L). Cells are then harvested. Fatty acids produced can be further isolated and/or analyzed.

In another aspect, the present disclosure is directed to a method for producing specific branched-chain fatty acid species. In one embodiment, the method includes providing a transformed host cell comprising a nucleic acid encoding a branched-chain α-keto acid dehydrogenase; a nucleic acid encoding a branched-chain-specific 3-Ketoacyl-(acyl-carrier-protein) Synthase III; a nucleic acid comprising a sequence encoding an acyl-CoA thioesterase I; and a nucleic acid encoding a lipoyl ligase A; and culturing the transformed host cell in a culture medium comprising lipoic acid and an α-keto acid, wherein the transformed host cell produces a specific branched-chain fatty acid species. In another embodiment, the method includes providing a transformed host cell comprising a nucleic acid comprising a sequence encoding a branched-chain α-keto acid dehydrogenase; a nucleic acid comprising a sequence encoding a branched-chain-specific β-ketoacyl-[acyl-carrier-protein] synthase III; a nucleic acid comprising a sequence encoding an Acyl-CoA thioesterase I; a nucleic acid comprising a sequence encoding a lipoyl (octanoyl) synthase (lipB); and a nucleic acid comprising a sequence encoding a lipoyl synthase (lipA); and culturing the transformed host cell in a culture medium, wherein the transformed host cell produces a specific branched-chain fatty acid species. The branched-chain-specific β-ketoacyl-[acyl-carrier-protein] synthase III is the only β-ketoacyl-[acyl-carrier-protein] synthase III. In particular, the straight-chain-specific FabH is deleted in the transformed host cell and functionally replaced with one of the branched-chain-specific FabHs. For example, the native fabH gene can be deleted and functionally replaced with a β-Ketoacyl-(acyl-carrier-protein) synthase III enzyme with high branched-chain acyl-CoA specificity.

Suitable α-keto acids can be selected from 3-methyl-2-oxobutyric acid, 4-methyl-2-oxopentanoic acid, 3-methyl-2-oxopentanoic acid and combinations thereof. Particularly suitable genes can be, for example, acetolactate synthase (alsS; Gene ID: 936852); ketol-acid reductoisomerase, NAD (P)-binding (ilvC, Gene ID: 948286); dihydroxyacid dehydratase (ilvD, Gene ID: 948277); 2-isopropylmalate synthase (leuA, Gene ID: 947465); 3-isopropylmalate dehydrogenase (leuB, Gene ID: 944798); 3-isopropylmalate dehydratase large subunit (leuC, Gene ID: 945076); 3-isopropylmalate dehydratase small subunit (leuD, Gene ID: 945642); and combinations thereof.

In one embodiment, when the α-keto acid is 3-methyl-2-oxobutyric acid, the specific branched-chain fatty acid species is an even-chain-iso branched-chain fatty acid species. In another embodiment, when the α-keto acid is 4-methyl-2-oxopentanoic acid, the specific branched-chain fatty acid species is an odd-chain iso branched-chain fatty acid species. In another embodiment, when the α-keto acid is 3-methyl-2-oxopentanoic acid and the specific branched-chain fatty acid species is an even-chain-anteiso branched-chain fatty acid species.

The nucleic acid encoding the branched-chain α-keto acid dehydrogenase can be obtained from any organism having the branched-chain α-keto acid dehydrogenase. In one embodiment, the nucleic acid encoding the branched-chain α-keto acid dehydrogenase can be obtained from *Bacillus subtilis* and *Staphylococcus aureus*, as described herein. In another embodiment, the nucleic acid encoding a branched-chain α-keto acid dehydrogenase has about 80%, about 85%, about 90%, about 95%, about 96%, about 97%, about 98%, and about 99% sequence identity to SEQ ID NO:1 (bkdAA Gene ID: 14770064), SEQ ID NO:2 (bkdAB Gene ID: 14770063), SEQ ID NO:3 (bkdB Gene ID:14770062) and SEQ ID NO:4 (lpdV Gene ID:14770065), as described herein.

In one embodiment, the nucleic acid encoding a lipoyl ligase A has about 80%, about 85%, about 90%, about 95%, about 96%, about 97%, about 98%, and about 99% sequence identity to SEQ ID NO:8 (Gene ID:944865) Lipoyl ligase A (EC 2.7.7.63), as described herein.

The transformed host cell further includes a nucleic acid encoding a β-Ketoacyl-(acyl-carrier-protein) Synthase III, as described herein. Particularly suitable β-Ketoacyl-(acyl-carrier-protein) synthase IIIs can be selected from $_{Sa}$FabH and $_{Bs}$FabH2, as described herein. In another embodiment, the nucleic acid encoding a $_{Sa}$FabH has about 80%, about 85%, about 90%, about 95%, about 96%, about 97%, about 98%, and about 99% sequence identity to SEQ ID NO:5 (*Staphylococcus aureus* Gene ID:23196764). In another embodiment, the nucleic acid encoding a $_{Bs}$FabH has about 80%, about 85%, about 90%, about 95%, about 96%, about 97%, about 98%, and about 99% sequence identity to SEQ ID NO:6 (*Bacillus subtilis* Gene ID:939306), as described herein.

The transformed host cell can further include a nucleic acid encoding a FadR (fatty acid degradation R), as described herein. In one embodiment, the nucleic acid encoding FadR has about 80%, about 85%, about 90%, about 95%, about 96%, about 97%, about 98%, and about 99% sequence identity to SEQ ID NO:9 (*E. coli* Gene ID:948652), as described herein.

Any microbial cell can be used as the transformed host cell as described herein. Particularly suitable transformed host cells can be transformed *Escherichia coli*.

A particularly suitable transformed *E. coli* host cell is one that overexpresses BKD in combination with TesA and a branch-chain-specific FabH, in which strain fabH is deleted from the parental *E. coli* MG1655 background (see, Lai and Cronan, J. Biol. Chem. Dec. 19, 2003; 278(51):51494-503, which is incorporated by reference herein).

For branched-chain fatty acid production, cells are cultured as described herein. For α-keto acid supplementation, one of the α-keto acids β-methyl-2-oxobutyric acid, 4-methyl-2-oxopentanoic acid, or 3-methyl-2-oxopentanoic acid) is supplemented in the minimal medium. Cells are then harvested. Fatty acids produced can be further isolated and/or analyzed.

Fatty acid titer can be determined using methods known to those skilled in the art. Suitably, a portion of the transformed host cell culture can be acidified with hydrochloric acid and extracted into ethyl acetate by mixing and centrifugation. The resultant organic layer can then be separated from the aqueous portion, which is discarded. Fatty acids can then be derivatized to fatty acid methyl esters with methanol, hydrochloric acid and trimethylsilane-diazomethane. The derivatized fatty acids can be analyzed using gas chromatography-mass spectrometry (GC-MS), for example. Fatty acid concentrations can be quantified by comparing the area of each fatty acid methyl ester peak to a standard curve generated by standard fatty acid methyl ester mixtures (for example, GLC-20, GLC-30, and Bacterial Acid Methyl Ester Mix, available from Sigma-Aldrich, St. Louis, Mo.) using nonadecanoic acid (Sigma-Aldrich, St. Louis, Mo.) as an internal standard.

Fatty acid species can be identified using methods known to those skilled in the art. Suitably, the fatty acid species produced according to the instant methods can be identified by comparing their retention times to those of standard commercially available branched-chain fatty acid methyl esters (for example, Bacterial Acid Methyl Ester Mix, available from Sigma-Aldrich, St. Louis, Mo.) and by comparing their mass spectra to the Probability Based Matching (PBM) Mass Spectrometry Library.

EXAMPLES

Materials

Phusion DNA polymerase was purchased from New England Biolabs (Beverly, Mass., USA). Restriction enzymes, T4 ligase, gel purification kits, and plasmid miniprep kits were purchased from Thermo Fisher Scientific (Waltham, Mass., USA). All primers were synthesized by Integrated DNA Technologies (Coralville, Iowa, USA). BCFA standards (Bacterial Acid Methyl Ester Mix), SCFA standards (GLC-20 and GLC-30), and all the other reagents were purchased from Sigma Aldrich (St. Louis, Mo., USA).

Plasmids and Strains.

Plasmids used in this study are listed in Table 1.

TABLE 1

Plasmids.

| Plasmids | Replication ori | Gene and promoter | Resistance | Reference |
|---|---|---|---|---|
| pA5k-tesA | p15a | $P_{lacUV5}$-tesA(*E. coli*) | $Kan^R$ | (Jiang W. et al. 2015) |
| pA5c-tesA | p15a | $P_{lacUV5}$-tesA(*E. coli*) | $Cm^R$ | This study |
| pA58c-tesA-fadR | p15a | $P_{lacUV5}$-tesA(*E. coli*), $P_{BAD}$-fadR(*E. coli*) | $Cm^R$ | This study |
| pSa-$P_{ecfabH\text{-}Bs}$fabH2 | SC101 | $P_{ecfabH}$-fabH2(*B. subtilis*) | $Amp^R$ | (Jiang W. et al. 2015) |
| pSa-$P_{ecfabH\text{-}Sa}$fabH | SC101 | $P_{ecfabH}$-fabH (*S. aureus*) | $Amp^R$ | (Jiang W. et al. 2015) |
| pB5c-tesA-bkd | pBBR1 | $P_{lacUV5}$-tesA(*E. coli*)-lpdV-bkdAA-bkdAB-bkdB (*B. subtilis*) | $Cm^R$ | (Jiang W. et al. 2015) |
| pA8k-fadR | p15a | $P_{BAD}$-fadR(*E. coli*) | $Kan^R$ | This study |
| pE8k-lplA | ColE1 | $P_{BAD}$-lplA(*E. coli*) | $Kan^R$ | This study |
| pA5k-fadR-lplA | p15a | $P_{lacUV5}$-fadR-lplA (*E. coli*) | $Kan^R$ | This study |
| pB5c-rfp | pBBR1 | $P_{lacUV5}$-rfp | $Cm^R$ | This study |
| pE8c-tesA-bkd | ColE1 | $P_{BAD}$-tesA(*E. coli*)-lpdV-bkdAA-bkdAB-bkdB (*B. subtilis*) | $Cm^R$ | This study |
| pA8k-lipA-lipB-fadR | p15a | $P_{BAD}$-lipA-lipB-fadR (*E. coli*) | $Kan^R$ | This study |
| pA8k-lipA-lipB* | p15a | $P_{BAD}$-lipA-lipB (*E. coli*) | $Kan^R$ | This study |
| pA58k-lipA-lipB*-isc | p15a | $P_{BAD}$-lipA-lipB-$P_{LacUV5}$-iscS-iscU-iscA-hscB-hscA-fdx-iscX | $Kan^R$ | This study |
| pE8c-tesA-mleuABCD | ColE1 | $P_{BAD}$-tesA-mleuABCD (*E. coli*) | $Cm^R$ | This study |
| pA6k-alsS-ilvCD (pSA69) | p15a | $P_{LlacO-1}$- alsS-ilvCD (*E. coli*) | $Kan^R$ | (Atsumi et al., 2008) |

All the plasmids were constructed using standard restriction digestion cloning based on the Biobrick platform as described previously (Lee et al., J Biol Eng. 2011; 5:12; Gibson et al., Nat. Methods 2009; 6:343-345).

*E. coli* DH10B was used for cloning purposes (see, Table 2). *E. coli* strains DH1(ΔfadE) and CL111 (Lai and Cronan, J. Biol. Chem. 2003; 278:51494-51503) were used for fatty acid production. Knockout *E. coli* fabH strains BC00-BC33F* using the CL111 background strain were generated as described in Jiang et al. (Biotech. and Bioeng., August 2015, 112(8):1613-1622).

TABLE 2

Strains.

| Strains | Relevant genotype | fabH gene | Reference |
|---|---|---|---|
| CL111 | UB1005, attHK022::(plsX⁰ fabH, Spc$^R$ Str$^R$), fabH::Kan | $_{Se}$fabH | (Lai et al. 2003) |
| CAG12094 | MG1655, zcb-3059::Tn10 | $_{Ec}$fabH | (Jiang et al. 2010) |
| SC01 | DH1 (ΔfadE) pA5k-tesA | $_{Ec}$fabH | This study |
| SC02 | DH1 (ΔfadE) pB5c-rfp, pA5k-tesA | $_{Ec}$fabH | This study |
| SC03 | DH1 (ΔfadE) pE8c-tesA-bkd | $_{Ec}$fabH | This study |
| BC11 | CL111 (plsX'fabH; aadA)::Tet$^4$ pSa-P$_{ecfabH\text{-}Bs}$fabH2 | $_{Bs}$fabH2 | (Jiang W. et al. 2015) |
| BC13 | CL111 (plsX'fabH; aadA)::Tet$^4$ pSa-P$_{ecfabH\text{-}Sa}$fabH | $_{Sa}$fabH | (Jiang W. et al. 2015) |
| BC11A | CL111 (plsX'fabH; aadA)::Tet$^4$ pSa-P$_{ecfabH\text{-}Bs}$fabH2, pB5c-tesA-bkd | $_{Bs}$fabH2 | (Jiang W. et al. 2015) |
| BC11L | CL111 ((plsX'fabH; aadA)::Tet$^4$, ΔKan, pSa-P$_{ecfabH\text{-}Bs}$fabH2, pB5c-tesA-bkd, pE8k-lplA | $_{Bs}$fabH2 | This study |
| BC11F | CL111 ((plsX'fabH; aadA)::Tet$^4$, ΔKan, pSa-P$_{ecfabH\text{-}Bs}$fabH2, pB5c-tesA-bkd, pA8k-fadR | $_{Bs}$fabH2 | This study |
| BC13A | CL111 (plsX'fabH; aadA))::Tet$^4$ pSa-P$_{ecfabH\text{-}Sa}$fabH, pB5c-tesA-bkd | $_{Sa}$fabH | (Jiang W. et al. 2015) |
| BC13L | CL111 (plsX'fabH; aadA)::Tet$^4$, ΔKan, pSa-P$_{ecfabH\text{-}Sa}$fabH, pB5c-tesA-bkd, pE8k-lplA | $_{Sa}$fabH | This study |
| BC31A | CL111 (plsX'fabH; aadA)::Tet$^4$ pSa-P$_{ecfabH\text{-}Sa}$fabH, pB5c-tesA-bkd | | |
| BC13FL | CL111 (plsX'fabH; aadA)::Tet$^4$, ΔKan, pSa-P$_{ecfabH\text{-}Sa}$fabH, pE8c-tesA-bkd, pA5k-fadR-lplA | $_{Sa}$fabH | This study |
| BC53A | CL111 (plsX'fabH; aadA)::Tet$^4$, ΔKan, pSa-P$_{ecfabH\text{-}Sa}$fabH, pB5c-tesA-bkd, pA8k-lipA-lipB-fadR | $_{Sa}$fabH | This study |
| BC53B | CL111 (plsX'fabH; aadA)::Tet$^4$, ΔKan, pSa-P$_{ecfabH\text{-}Sa}$fabH, pB5c-tesA-bkd, pA8k-lipA-lipB* | $_{Sa}$fabH | This study |
| BC53C | CL111 (plsX'fabH; aadA)::Tet$^4$, ΔKan, pSa-P$_{ecfabH\text{-}Sa}$fabH, pB5c-tesA-bkd, pA58k-lipA-lipB*-isc | $_{Sa}$fabH | This study |
| BC33 | CL111 (plsX'fabH, aadA)::Tet$^4$, ΔKan, fadE::bkd, ldhA::fadR-lplA, pSa-P$_{ecfabH\text{-}Sa}$fabH, pE8c-tesA-mleuABCD, pA6k-alsS-ilvCD | $_{Sa}$fabH | This study |
| BC33A | CL111 (plsX'fabH; aadA)::Tet$^4$, ΔKan, fadE::bkd, pSa-P$_{ecfabH\text{-}Sa}$fabH, pA5k-tesA | $_{Sa}$fabH | This study |
| BC33L | CL111 (plsX'fabH; aadA)::Tet$^4$, ΔKan, fadE::bkd, pSa-P$_{ecfabH\text{-}Sa}$fabH, pA5k-tesA, pE8k-lplA | $_{Sa}$fabH | This study |
| BC33FL | CL111 (plsX'fabH; aadA)::Tet$^4$, ΔKan, fadE::bkd, pSa-P$_{ecfabH\text{-}Sa}$fabH, pA58c-tesA-fadR, pE8k-lplA | $_{Sa}$fabH | This study |
| BC31A | CL111 (plsX'fabH; aadA)::Tet$^4$, ΔKan, fadE::bkd, pSa-P$_{ecfabH\text{-}Bs}$fabH2, pA5c-tesA | $_{Bs}$fabH2 | This study |

Cell Culture and FA Production.

Cells were pre-cultivated in LB medium with relevant antibiotics: kanamycin (50 mg/L), ampicillin (100 mg/L), and chloramphenicol (30 mg/L). Overnight cultures were inoculated 2% v/v into modified M9 minimal medium with 2% glucose with corresponding antibiotics for adaptation. Overnight cultures in minimal medium were then used to inoculate 5 mL of the same fresh minimal medium with an initial $OD_{600}$ of 0.08-1.0. Cells were induced with relevant inducers (1 mM Isopropyl β-D-1-thiogalactopyranoside (IPTG), 0.4% arabinose, or otherwise specified) when $OD_{600}$ reached 0.8-1.0. For α-keto acids supplementation experiments, one of the α-keto acids β-methyl-2-oxobutyric acid, 4-methyl-2-oxopentanoic acid, or 3-methyl-2-oxopentanoic acid) was supplemented at 1 g/L unless otherwise specified. For transformed host cells including LipB and LipA, cells were induced when $OD_{600}$ reached 0.8-1.0. Cells were harvested 72 hours after induction and analyzed for FA production.

Cell growth curves were recorded on an Infinite F200PRO (TECAN) plate reader. Overnight LB cultures were used to inoculate modified M9 medium with 2% glucose. Overnight cultures were then used to inoculate 5 mL of the same fresh minimal medium with an initial $OD_{600}$ of 0.08. Upon inoculation, 150 μl of the culture was aliquoted into a 96-well plate. The 5 mL culture was used for fatty acid quantification, while the 96-well plate was incubated inside the plate reader with shaking (218.3 rpm, 37° C.) to record cell growth. Relative cell density (in arbitrary units) was measured by monitoring absorption at 600 nm. Data were taken every 1500 seconds until the cell culture reached late stationary phase Quantification of Free Fatty Acids.

Titers of free fatty acids were quantified using a previously published method (Jiang et al 2015). Briefly, 1 mL of whole culture was acidified with 12 N HCl, and extracted into ethyl acetate by vortexing and centrifugation. The organic layer was isolated and fatty acids were derivitized to fatty acid methyl esters (FAMEs) with methanol, HCl, and trimethylsilane-diazomethane. Derivatized fatty acids were analyzed using a GC-MS (Hewlett-Packard model 7890A, Agilent Technologies) equipped with a 30 m DB5-MS column (J&W Scientific) and a mass spectrometer (5975C, Agilent Technologies) or a FID (Agilent Technologies) detector. BCFA species were identified by comparing their retention times to those of standard BCFA methyl esters (Bacterial Acid Methyl Ester Mix, Sigma Aldrich) and by comparing their mass spectra to the Probability Based Matching (PBM) Mass Spectrometry Library. FA concentrations were quantified by comparing the area of each FAME peak to a standard curve generated by standard FAME mixtures (GLC-20, GLC-30, and Bacterial Acid Methyl Ester Mix, Sigma Aldrich) using nonadecanoic acid (Sigma) as an internal standard. BCFA titer for each strain was measured in biological triplicate (starting from three different colonies) and average values are reported.

Membrane Lipid Analysis.

FFAs were first extracted and removed as described in 2.4. Membrane lipids were then extracted and analyzed following a published protocol (Folch et al., J. Biol. Chem. 1957; 226:497-509). Briefly, the aqueous layer containing membrane lipid after FFA removal was lyophilized (Labconco FreeZone 2.5 Liter Benchtop Freeze Dry System) for 2 hours at full vacuum and refrigeration, or until cells were completely desiccated. The pellets were then dissolved in 1 mL chloroform and 1 mL of 15% (v/v) $H_2SO_4$/methanol and heated at 100° C. for 3 hours for transesterification. Reaction mixtures were then cooled on ice for 5 minutes, followed by the addition of 1 mL purified water and vigorous shaking for 5 minutes. Organic phase containing FAMEs were then isolated and injected to GC-FID for analysis.

Growth on FA as the Sole Carbon Source.

M9 minimal medium was prepared with 1 mg/mL palmitic acid, 14-methyl-pentadecanoic acid, or 2% glucose as the sole carbon sources as previously described (Feng and Cronan, 2009). E. coli MG1655 and E. coli DH1 ΔfadE were first cultivated in LB medium to exponential growth phase. Media was then removed by centrifugation, and cells were rinsed with phosphate buffered saline three times. Rinsed cells were next resuspended in M9 minimal medium containing one of the above-described carbon sources at a density of $OD_{600}$=0.6. Cells were then cultivated at 37° C. and cell growth was monitored using an Infinite F200PRO Plate Reader (TECAN) for 72 hours.

Western Blotting and Protein Analysis. Whole culture, volume normalized by optical density at 600 nm, was incubated with loading buffer (2× Laemmli Sample Buffer (Bio-Rad) and β-mercaptoethanol) at 99° C. for 10 minutes with vigorous shaking. Then, 15 µl of whole culture lysates was loaded onto two 12% polyacrylamide denaturing gels and separated by electrophoresis. Gels were duplicated and run in parallel. One gel was then stained with Coomassie blue and the other was immunoblotted. For immunoblotting, protein was blotted to a polyvinylidine fluoride (PVDF) membrane. Lipoate modified enzymes were detected using a rabbit-anti-lipoyl primary antibody (EMD-Millipore) followed by a goat-anti-rabbit secondary antibody conjugated to horseradish peroxidase (Santa Cruz Biotechnology). Stained membranes were imaged using a GE ImageQuant (LAS 4000 mini).

Example 1

In this Example, the impact of BKD on cellular lipoylation was analyzed.

Figures 2A, 2B:
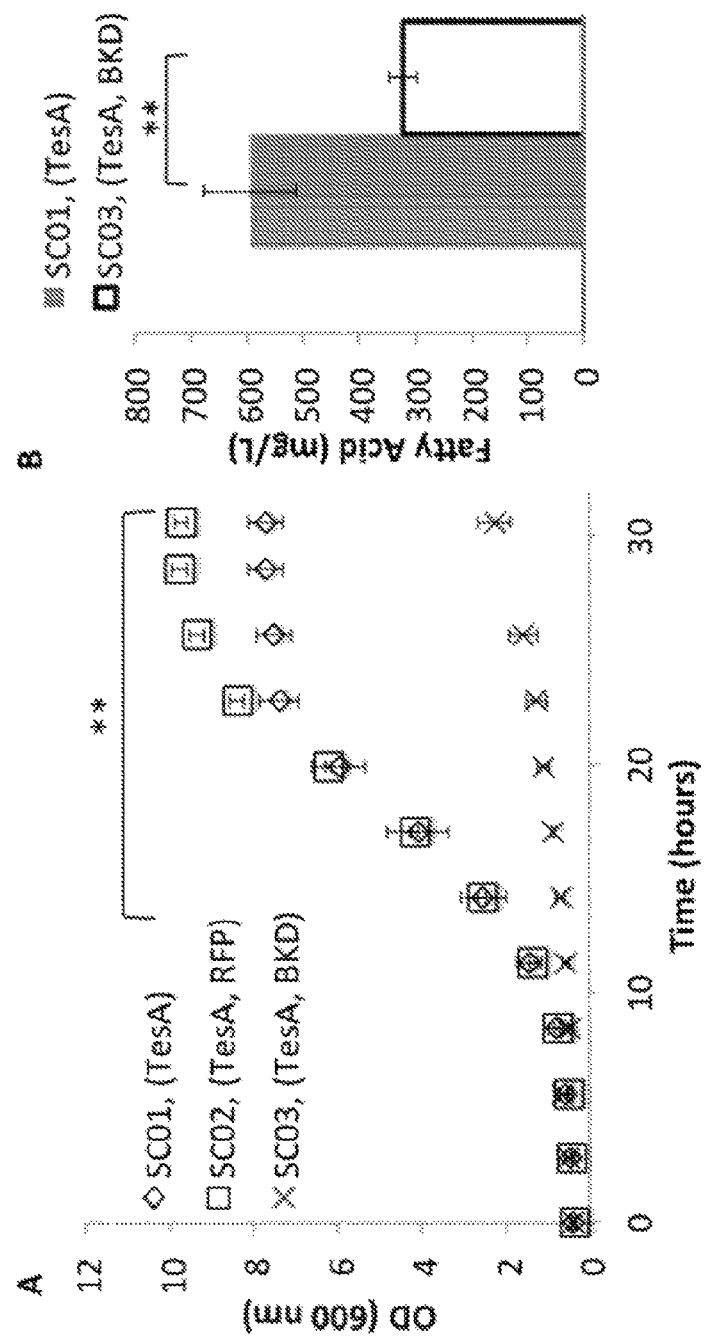
FIGS. 2A & 2B depict the reduction in cell growth and FA production by the expression of BKD.

A FFA-overproducing strain, SC01 (Tables 1 and 2), was first constructed by overexpressing a cytosolic thioesterase (TesA) in a fadE deleted E. coli DH1 strain. Next the Bacillus subtilis BKD was introduced to strain SC01, resulting in strain SC03. Overexpression of BKD significantly reduced cell growth when compared to strain SC01, p<0.01 (FIG. 2A). Expression of a red fluorescent protein (RFP, strain SC02) did not affect cell growth, indicating that the impaired cell growth was likely not caused by metabolic burden from protein expression. When strains SC01 and SC03 were cultivated for FFA production, a significant reduction in total FFA occurred with BKD overexpression, indicating that BKD expression also inhibits total FFA production (FIG. 2B).

Figure 3A:
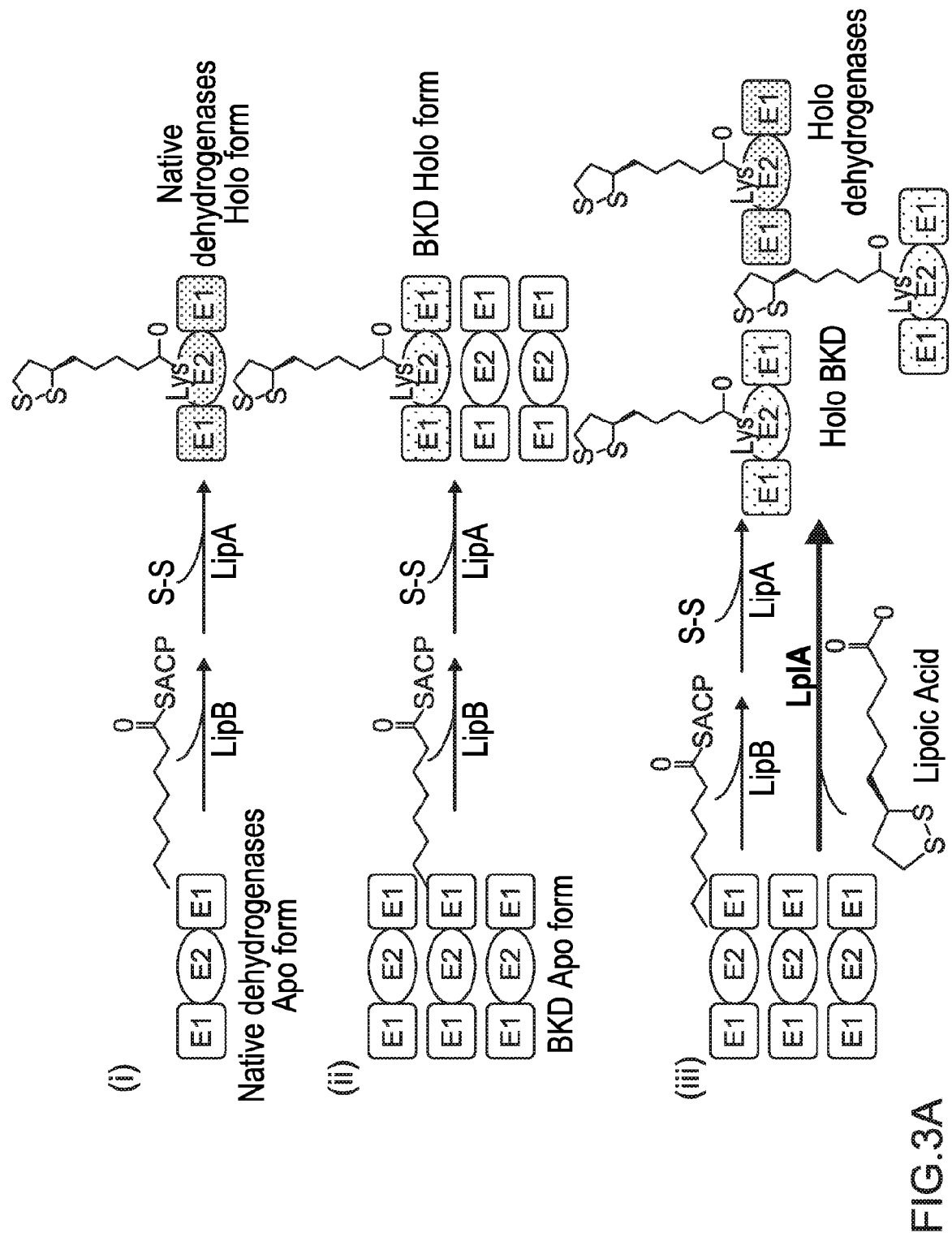
FIGS. 3A & 3B depict results demonstrating that the expression of BKD results in reduced enzyme lipoylation.

Overexpression of the PDH E2 subunit in E. coli represses PDH activity, suggesting that E. coli has limited protein lipoylation capacity. Expression of BKD requires lipoylation of its E2 subunit, which might similarly deplete the cellular lipoylation capability, leading to unlipoylated PDH and OGD in addition to under-lipoylated BKD (FIG. 3A). Because both PDH and OGD catalyze cell growth-intrinsic reactions, overexpression of BKD without expanding the host's lipoylation capacity may restrict lipoylation of PDH and OGD, resulting in the observed growth defect and reduced FA production.

Figure 3B:
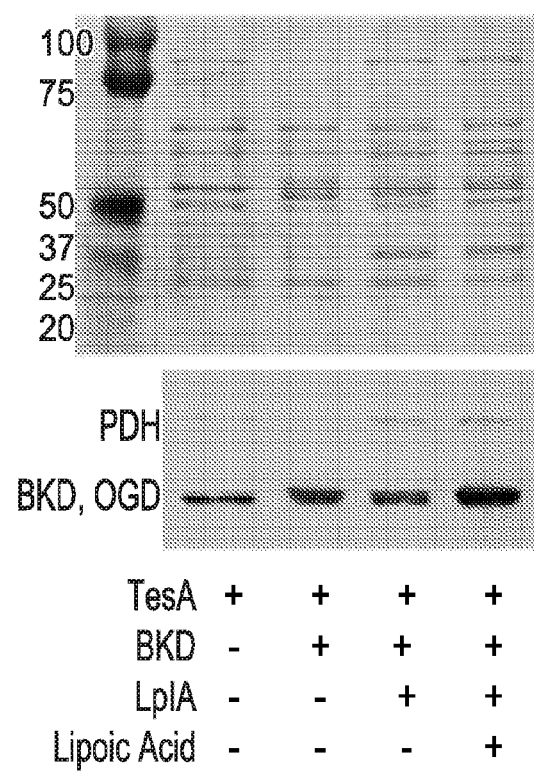

Whole cell lysates of strains with (SC03) or without BKD (SC01) overexpression were analyzed by SDS-PAGE and Western Blot using an anti-lipoyl-protein monoclonal antibody (FIG. 3B). The strain without BKD expression showed lipoylated proteins at sizes corresponding to the PDH E2 subunit (62 kDa) and the OGD E2 subunit (44 kDa, lane 1 in FIG. 3B). Strain SC03 with BKD overexpression showed a strong lipoyl-protein band corresponding to the size of the BKD E2 subunit (45 kDa, cannot be resolved with the 44 kDa OGD E2), but the previously visible band of lipoylated-PDH E2 disappeared (Lane 2 in FIG. 3B). Overall, the data revealed that BKD overexpression depleted protein lipoylation of E. coli native OADHs, leading to impaired cell growth (FIG. 2A) and reduced FA production (FIG. 2B).

Example 2

In this Example, the LplA was expressed for analyzing its effect on BCFA production.

The protein lipoylation deficiency caused by BKD overexpression was overcome by engineering a protein lipoylation pathway. E. coli utilizes two pathways for protein lipoylation (FIG. 3A). The first pathway synthesizes lipoate de novo, for which an octanoyl-moiety from octanoyl-ACP is transferred to an E2 subunit by LipB, followed by insertion of two sulfur atoms into the octanoyl side chain of an octanolyated E2 domain by LipA, forming a five membered ring. Alternatively, exogenous lipoic acid can be ligated directly to an E2 subunit by lipoyl protein ligase A (LplA, encoded by lplA). A strain was engineered to utilize exogenous lipoic acid, in order to maximize the amount of octanoyl-ACP available for fatty acid elongation. lplA under the control of a $P_{BAD}$ promoter was cloned and transformed to the previously-described BCFA-producing strain, BC11A (CL111 (plsX'fabH; aadA):Tet$^4$ pSa-$P_{EcfabH-Bs}$fabH2, pB5c-tesA-bkd; Table 2), resulting in strain BC11L. Western Blotting of lipoyl proteins was used to examine whether the engineered lipoylation pathway was sufficient to restore native OADH lipoylation. As shown in FIG. 3B, overexpression of LplA alone recovered the lipoylated PDH E2 band to some extent, likely due to the secondary activity of LplA as an octanoate ligase (Lane 3 in FIG. 3B). Supplementation of lipoic acid to the LplA-expressing strain, completing the lipoylation pathway, further increased the intensity of the lipoylated PDH E2 band (Lane 4 in FIG. 3B). Meanwhile, intensity of the BKD E2 band also increased with LplA expression and lipoic acid supplementation, demonstrating that the engineered pathway improved lipoylation of not only PDH, but also BKD and potentially OGD.

Figure 4B:
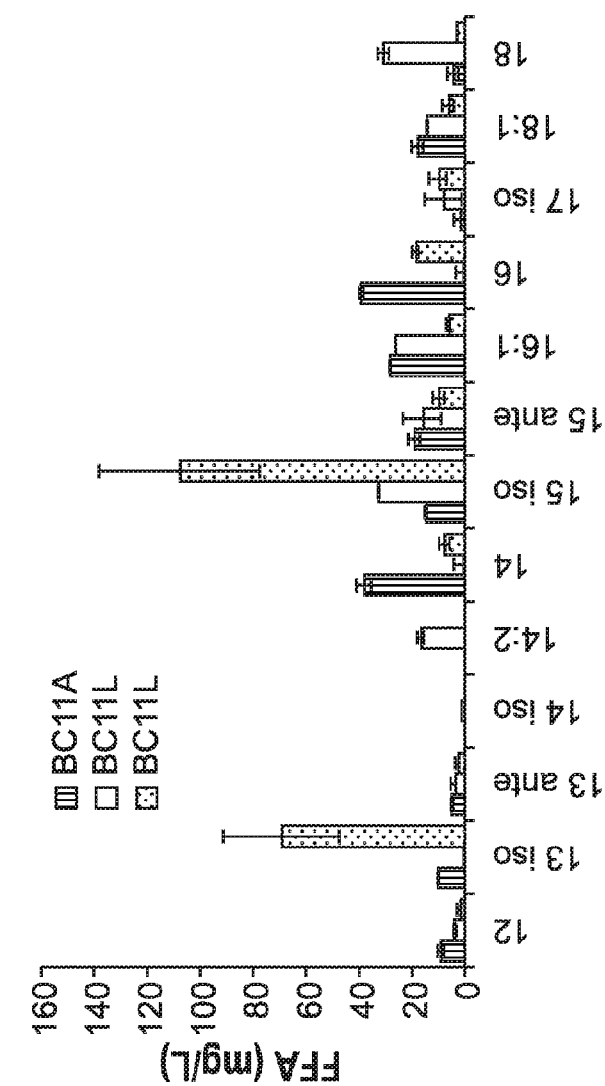
FIGS. 4A-4D depict an increased BCFA production by LplA expression with lipoic acid supplementation.
Figure 4A:
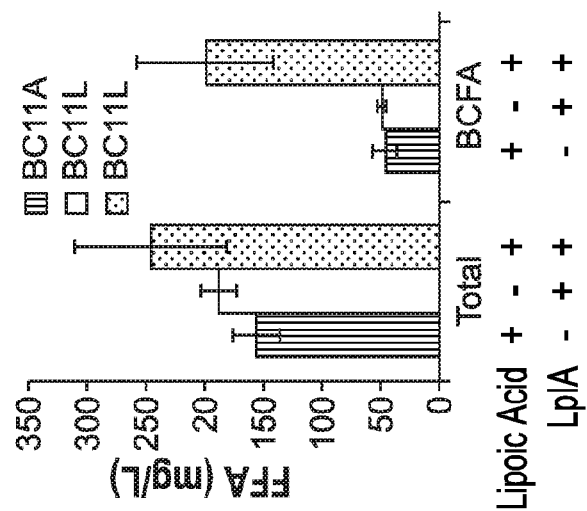
Figure 4D:
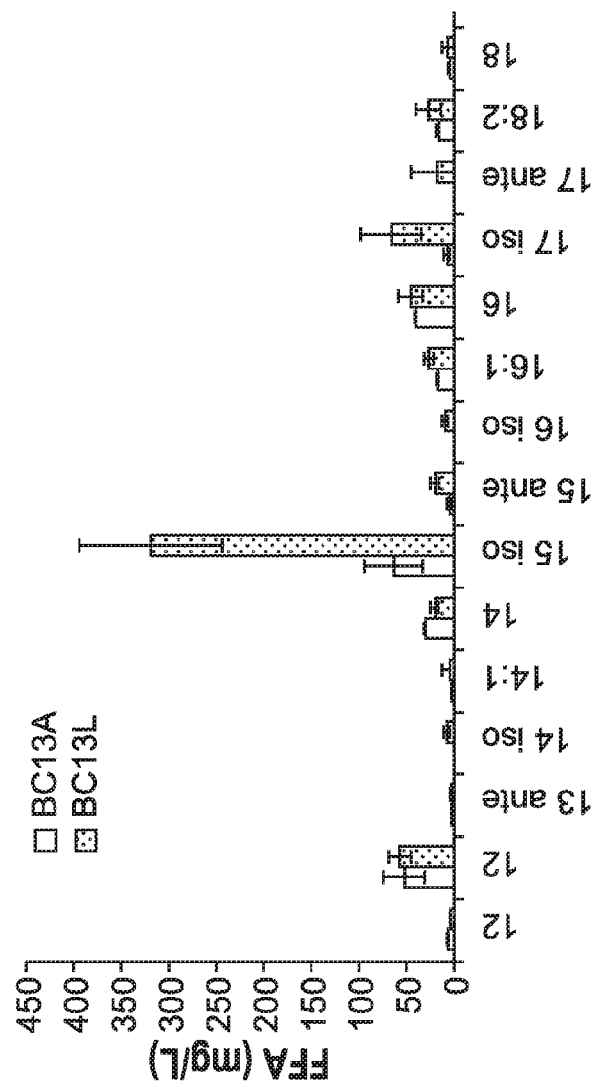
Figure 9A:
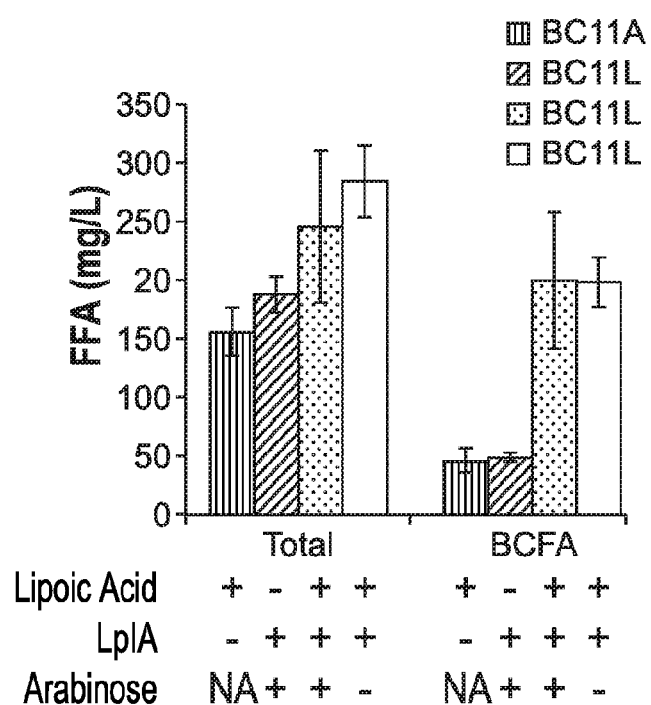
FIGS. 9A & 9B depict that lipoic acid alone was not sufficient to restore BCFA production.
Figure 9B:
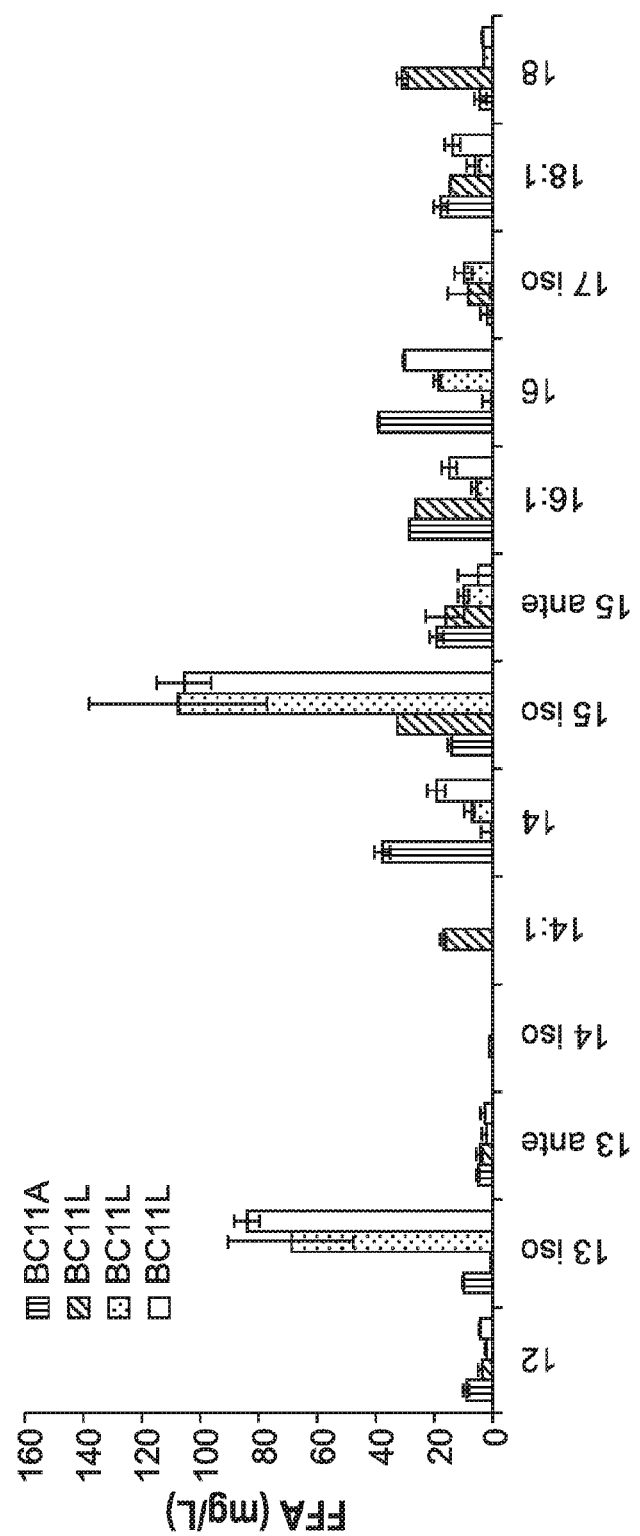

Whether lipoylation restoration in BC11L translates to increased BCFA titer and percentage was then examined. Without lipoic acid supplementation, strain BC11L produced 49 mg/L BCFA, statistically indistinguishable from its parental strain lacking LplA (BC11A, FIG. 4A). When lipoic acid was supplemented to strain BC11L, both total FFA and BCFA production increased dramatically. BCFA titer increased by 4-fold, reaching 200 mg/L, and the percentage of BCFA was increased from 29% in strain BC11A, to 81% in strain BC11L (FIG. 4A). The BCFA production in BC11L surpasses total FFA in the parental strain BC11A, indicating that lipoylation served to improve cellular capacity for FA production, either by improving cell fitness through native 2-oxoacid dehydrogenase lipoylation or by mediating toxicity of BKD. Among the produced BCFAs, odd-chain-iso FAs 11-methyldodecanoic acid (C13 iso) and 13-methyltetradecanoic acid (C15 iso) are the major products, representing 34% and 53% of total FFAs, respectively (FIG. 4B). Supplementation of lipoic acid to strain BC11A did not affect fatty acid production, indicating that lipoic acid alone is not sufficient to rescue lipoylation depletion caused by BKD overexpression (FIGS. 9A & 9B). Leaky expression of LplA in cultures without arabinose (the inducer of lplA expression) generated similar amount of BCFAs as when LplA was induced, indicating that even minimal overexpression of LplA was sufficient to lipoylate OADHs (FIGS. 9A & 9B), consistent to its role as a protein-modifying enzyme rather than a metabolic enzyme. These results demonstrated that engineering the protein lipoylation pathway alleviated cellular toxicity caused by BKD overexpression and promoted BKD lipoylation, leading to enhanced BCFA production and a significant increase in BCFA percentage.

Example 3

In this Example, the expression of $_{Sa}$FabH was analyzed for improvement of BCFA production.

Figure 4C:
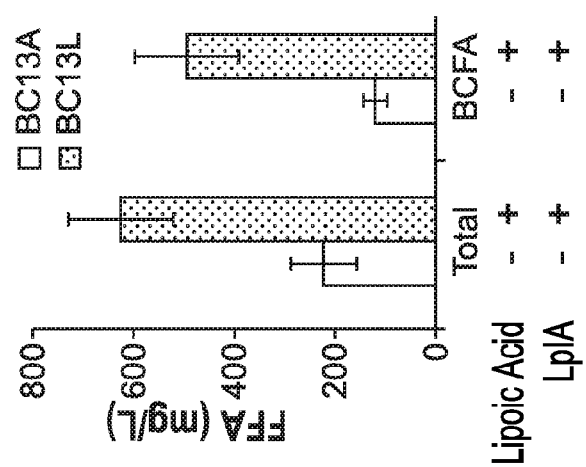

Whether the engineered lipoylation pathway would further increase BCFA production in a $_{Sa}$FabH-containing strain was tested. Strain BC13L was constructed expressing LplA in strain BC13A, which contains $_{Sa}$FabH as the sole FabH. While BC13A produced 120 mg/L BCFA, corresponding to 52% of total FFA, BC13L produced 494 mg/L BCFA, representing 79% of total FFA produced under the same cultivation conditions (FIG. 4C). The predominant product was 13-methyltetradecanoic acid (C15 iso, 318 mg/L), representing 50% of total FFAs. These results demonstrated that the engineered E. coli produced BCFAs in high titers (up to 494 mg/L) and high percentage (up to ~80%). Significantly, the results also demonstrated the high percentage BCFA production in E. coli, which would be difficult if high proportions of BCFA restricted SCFA availability for membrane construction.

Example 4

In this Example, bkd was integration into the genome to determine the effect on BKD toxicity.

To mediate the observed BKD toxicity, BKD was integrated into the genome. One strategy to reduce BKD toxicity was to integrate bkd into the E. coli genome, which reduced BKD copy number to alleviate potential metabolic burden, but also decreased any genetic instability associated with plasmid-borne BKD. BC33A contained bkd on the genome at the fadE locus under the control of a $P_{LacUV5}$ promoter and expresses $_{Sa}$FabH, as well as cytosolic TesA. Compared to the corresponding strain with plasmid-borne BKD (BC13A), integration of bkd into the genome did not increase BCFA production. Rather, BCFA titer dropped from 120 mg/L and 52% of total FFA in BC13A, to 20 mg/L and 31% BCFA in BC33A (FIG. 5), indicating that genomic BKD was insufficient for BCFA production. However, when the lipoylation pathway was restored by overexpression of LplA in the bkd-integrated strain (BC33L), BCFA production increased to 62 mg/L and 51% of total FFA (FIG. 5). These data indicate that genomic expression of bkd did not provide sufficient BCCSs to compete with acetyl-CoA, resulting in lower BCFA titers and percentage. However, even in the case of insufficient BKD, engineering the lipoylation pathway enhanced BCFA titer and percentage.

Example 5

In this Example, FadR and LplA were co-expressed to determine the effect on FFA and BCFA production.

Overexpression of the FA transcriptional regulator FadR increases total FFA production by activating expression of FA biosynthetic genes and repressing expression of β-oxidation genes. Whether expression of FadR could likewise increase BCFA production was tested. Strain BC13F was engineered to express ectopic BKD, $_{Sa}$FabH, TesA, and FadR and was compared to strain BC13A with the same background, but lacking FadR overexpression.

Figure 5A:
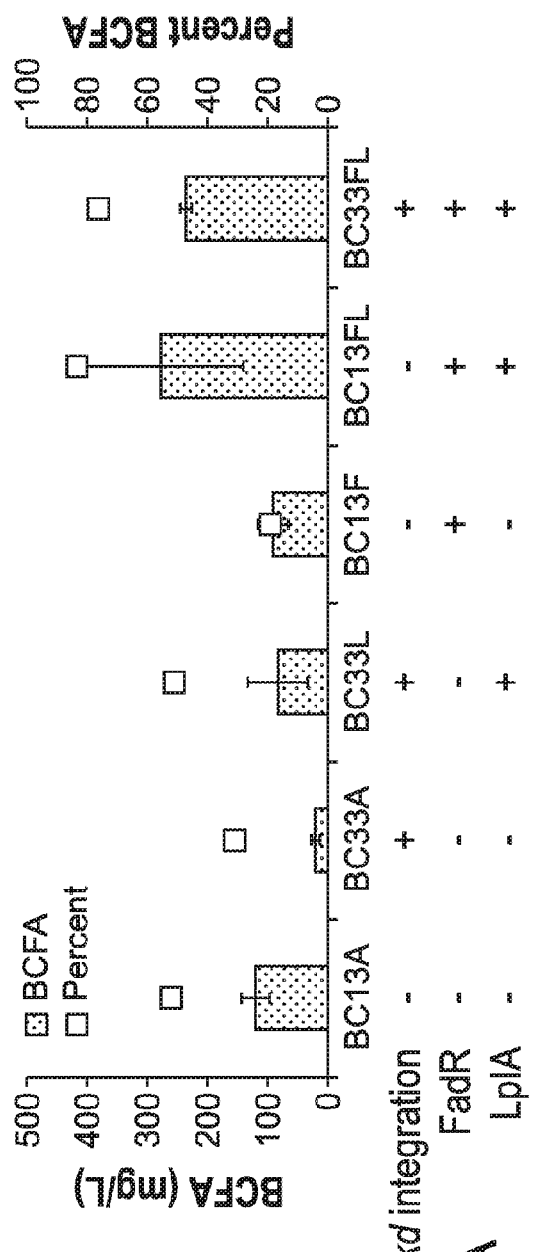
FIGS. 5A & 5B depict the strategies used to improve BCFA production.
Figure 5B:
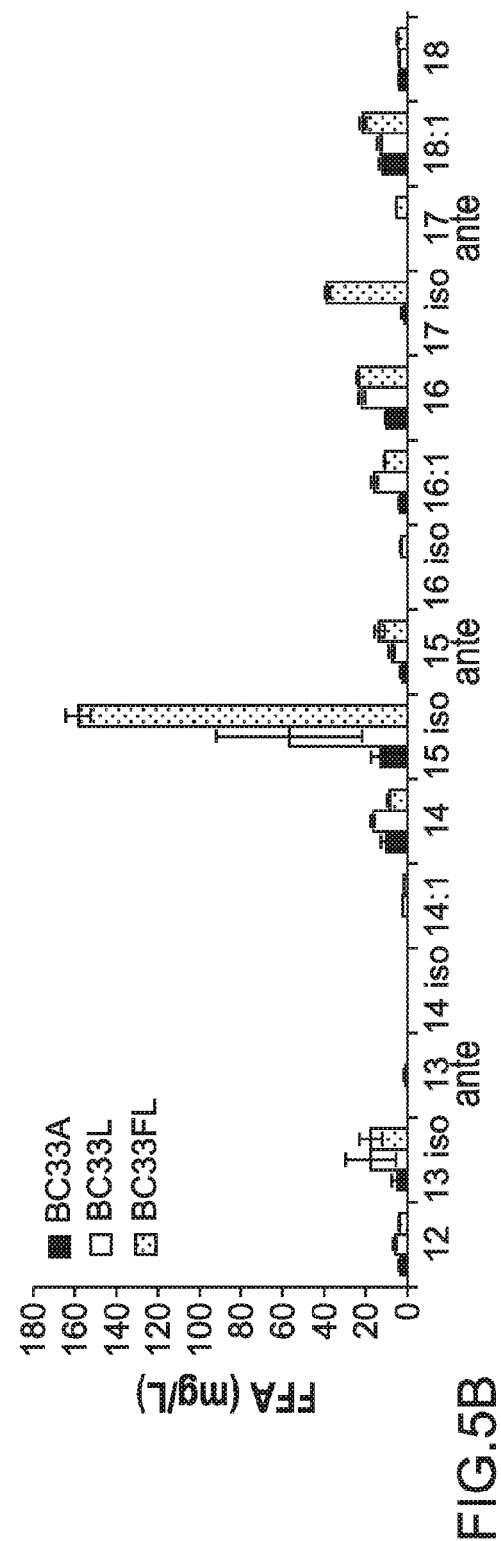
Figures 10A, 10B:
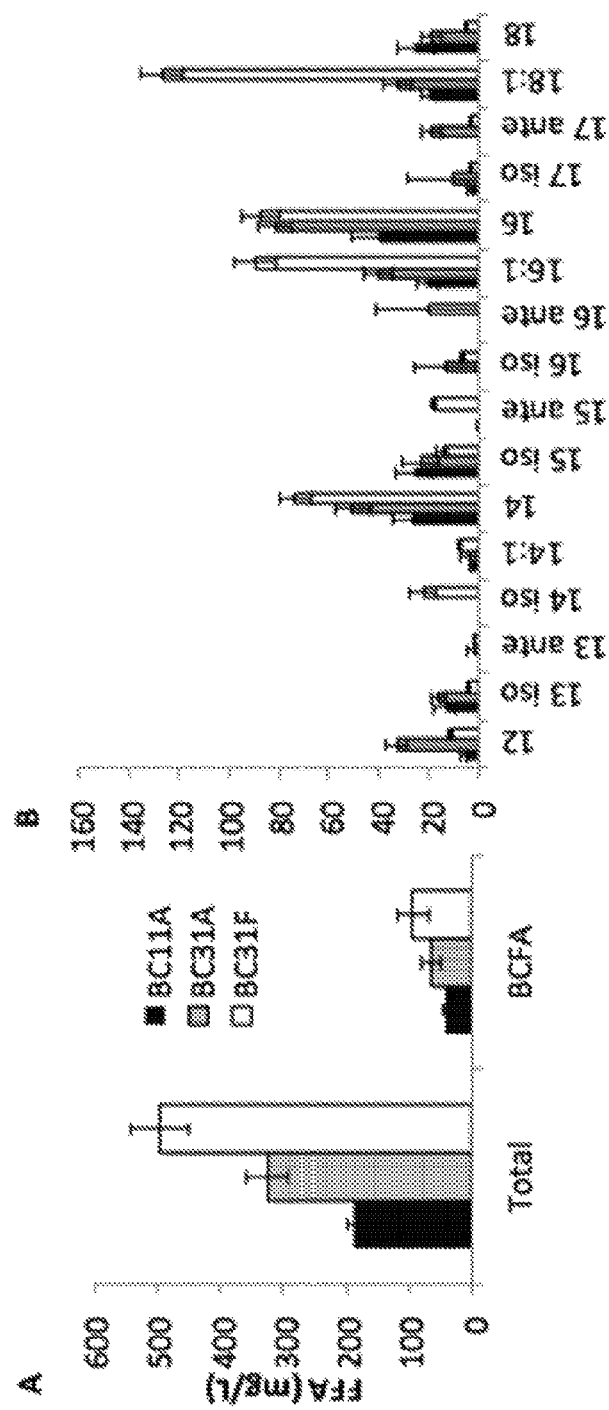
FIGS. 10A & 10B depicts the increase in unsaturated fatty acids by FadR expression.

FadR overexpression increased unsaturated fatty acid production (FIGS. 10A & 10B), but produced a similar amount of BCFAs, thus leading to a lower BCFA percentage in BC13F due to higher total FFAs (FIG. 5A). Next, the lipoylation pathway was introduced into BC13F, yielding strain BC13FL. Co-expression of FadR and LplA in BC13FL produced 235 mg/L of BCFA, reaching 83% of total FFA (FIG. 5A). In this case, 13-methyltetradecanoic acid (C15 iso) comprised 51% of total FFA. These results indicate that engineering the lipoylation pathway was the most effective method tested to increase BCFA production, where other strategies, such as bkd genome-integration and FadR expression, did not enhance BCFA production as efficiently as engineering the lipoylation pathway.

Example 6

In this Example, whether the chain structure of produced BCFAs can be controlled by the supply of α-ketoacid precursors was determined.

Figures 6A, 6B:
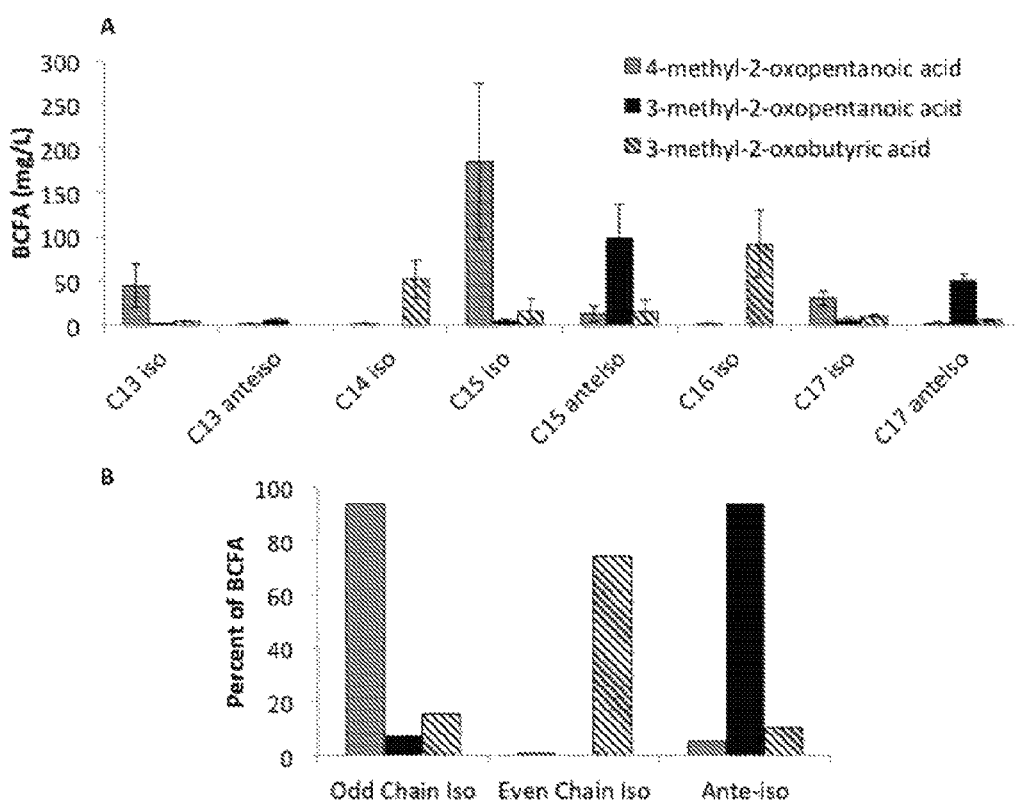
FIGS. 6A and 6B depict the control of branch position of BCFAs. Strain BC13FL was supplemented with 1 g/L of 4-methyl-2-oxopentanoic acid, 3-methyl-2-oxopentanoic acid, or 3-methyl-2-oxobutyric acid.

Cultures were supplemented with various α-ketoacids to determine the capacity of downstream pathways to produce BCFAs with tunable branch positions. Strain BC13FL was cultured and supplemented with 3-methyl-2-oxobutyric acid, 4-methyl-2-oxopentanoic acid, or 3-methyl-2-oxopentanoic acid. BCFA production strictly mirrored the branch structure of the supplemented α-ketoacid, generating even-chain-iso-FAs, odd-chain-iso-FAs, and odd-chain-anteiso-FAs as the major products, respectively (FIG. 6). Under all conditions, BCFA production exceeded 83% of total FFA. Specifically, when supplemented with 4-methyl-2-oxopentanoic acid, 93% of BCFA were odd-chain iso FFA. Likewise, when supplemented with 3-methyl-2-oxopentanoic acid or 3-methyl-2-oxobutyric acid, 93% and 74% of BCFA produced were even-chain-anteiso or even-chain-iso FFA, respectively. These results demonstrate position of the branch in BCFAs can be controlled by the supply of α-ketoacid precursors. When coupled with upstream α-ketoacid biosynthetic pathways, BCFAs with tailored branch position can be potentially produced from glucose.

Example 7

In this Example, the membrane composition of high percentage BCFA-producing strains was investigated.

Figures 7A, 7B:
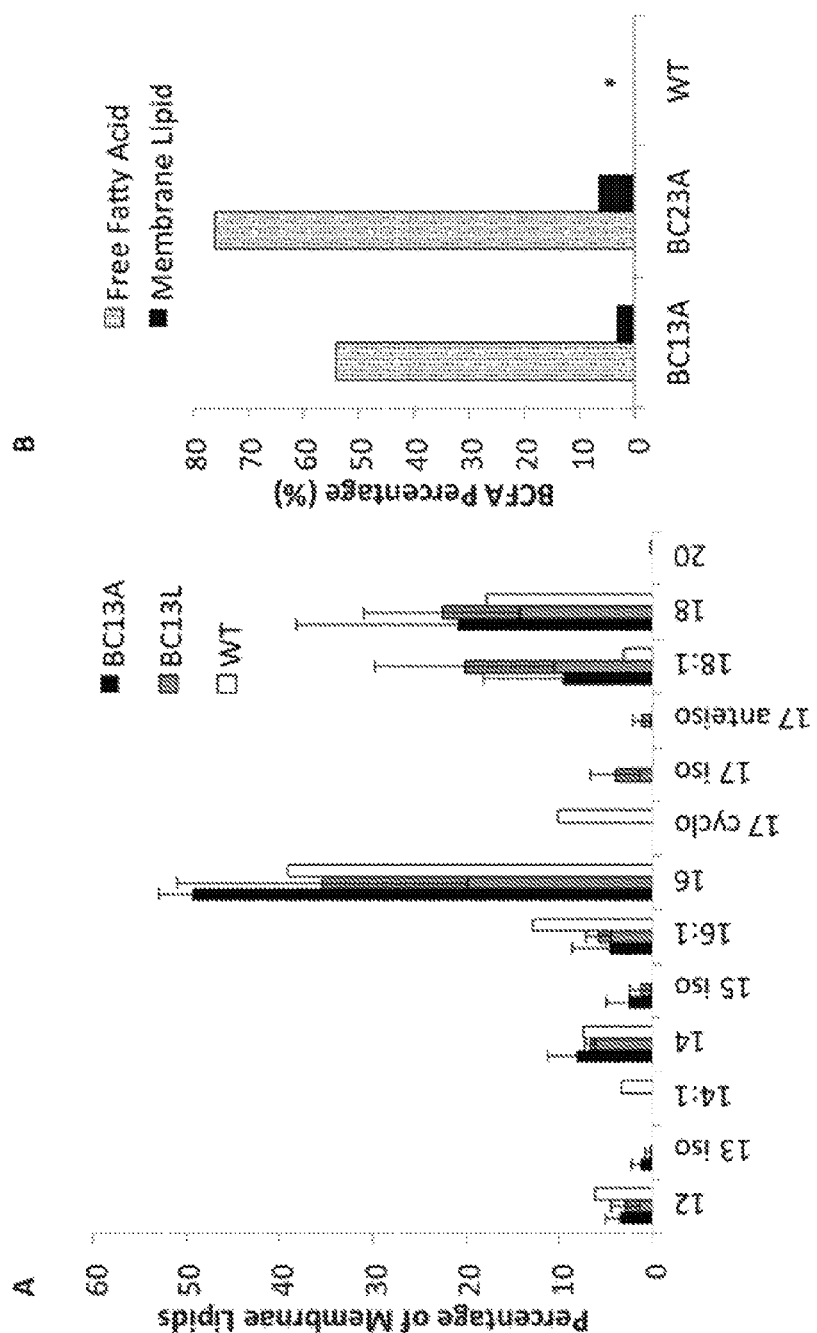
FIGS. 7A & 7B depict the membrane lipid composition of BCFA-producing strains.

While some Gram-positive bacteria alter the branched-chain content of their membranes to modulate fluidity, membranes of wild-type E. coli are composed strictly of SCFAs. If BCFAs produced from engineered pathways become incorporated into E. coli membrane lipids, they may alter the cell membrane fluidity and cause cellular stress or may be exported without membrane incorporation. Thus, whether any BCFA produced in high percentage was incorporated into the lipid membrane was determined. The membrane FA composition of engineered strains BC13L (produced 494 mg/L and 79% BCFA) and BC13A (produced 120 mg/L and 52% BCFA) were analyzed (FIG. 7). The method was first validated by measuring the membrane FA profile of wild-type E. coli; the obtained membrane FA profile was consistent with previous characterizations (FIG. 7). Next, the membrane profiles of strains BC13L and BC13A were analyzed. Membrane FA profiles of BCFA-generating strains were comparable to wild-type *E. coli*, with negligible incorporation of BCFAs into the cell membrane and no major shifts in the content of unsaturated FAs or chain length distribution (FIG. 7).

Figure 8A:
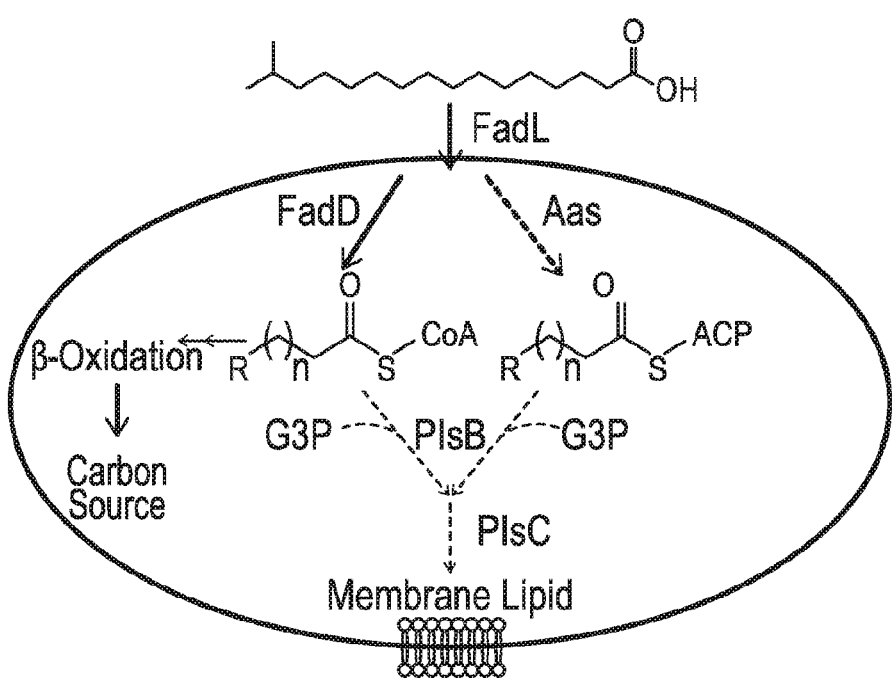
FIGS. 8A & 8B depict the growth of *E. coli* MG1655 on BCFA as sole carbon source.

The mechanism restricting BCFA from membrane incorporation was then determined. Extracellular FAs are transported into cells by FadL and are activated either to acyl-CoAs by the acyl-CoA synthetase (FadD), or to acyl-ACPs by the acyl-ACP synthase (AAS, encoded by aas). Fatty acyl-CoAs have two fates (FIG. 8A): they can be incorporated into phospholipids by PlsB/PlsC, or undergo β-oxidation to be utilized as a carbon source. Acyl-ACPs may also be incorporated into phospholipids by PlsB/PlsC. If BCFAs are restricted from membrane incorporation by FadL or FadD, they cannot be metabolized as a carbon source. If restriction does not occur at this step, BCFA membrane incorporation must be restricted by enzymes downstream of FadD, i.e., PlsB/PlsC (FIG. 8A).

Figure 8B:
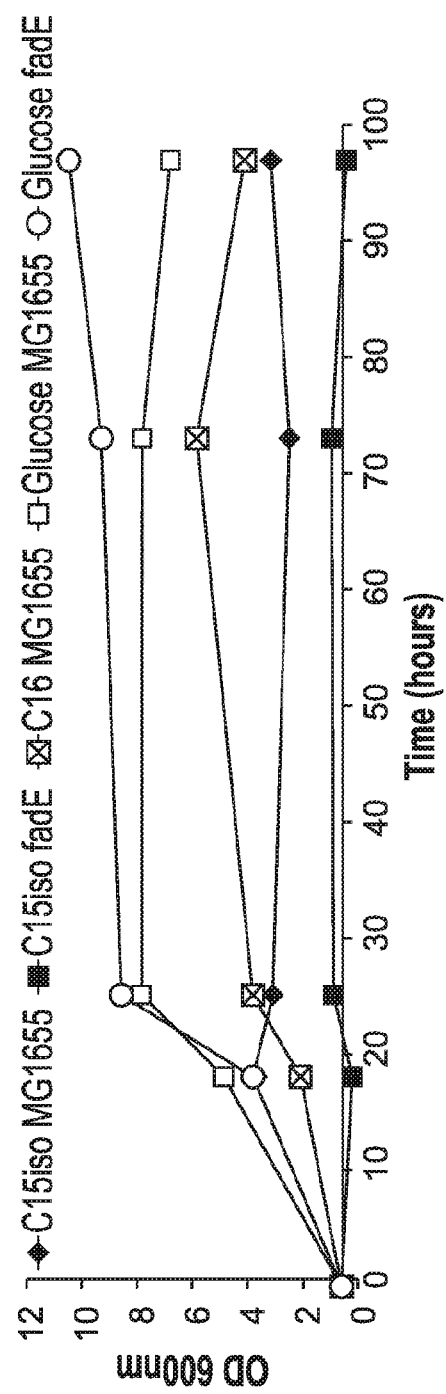

To elucidate the restriction mechanism, *E. coli* MG1655 was cultivated in media containing 13-methyltetradecanoic acid (C15-iso, the most abundant BCFA species produced in the engineered strains) as the sole carbon source. *E. coli* grew with 13-methyltetradecanoic acid as the sole source of carbon (although at a slower rate than that in palmitic acid, FIG. 8B), indicating that BCFAs are substrates of both FadL and FadD (FIG. 8). This finding indicated that restriction of BCFA from membrane incorporation occurs downstream of FadD, likely at AAS and/or the PlsB/PlsC step.

Example 8

In this Example, the production of branched-chain fatty acid ethyl esters (FAEE) was investigated.

Figure 11:
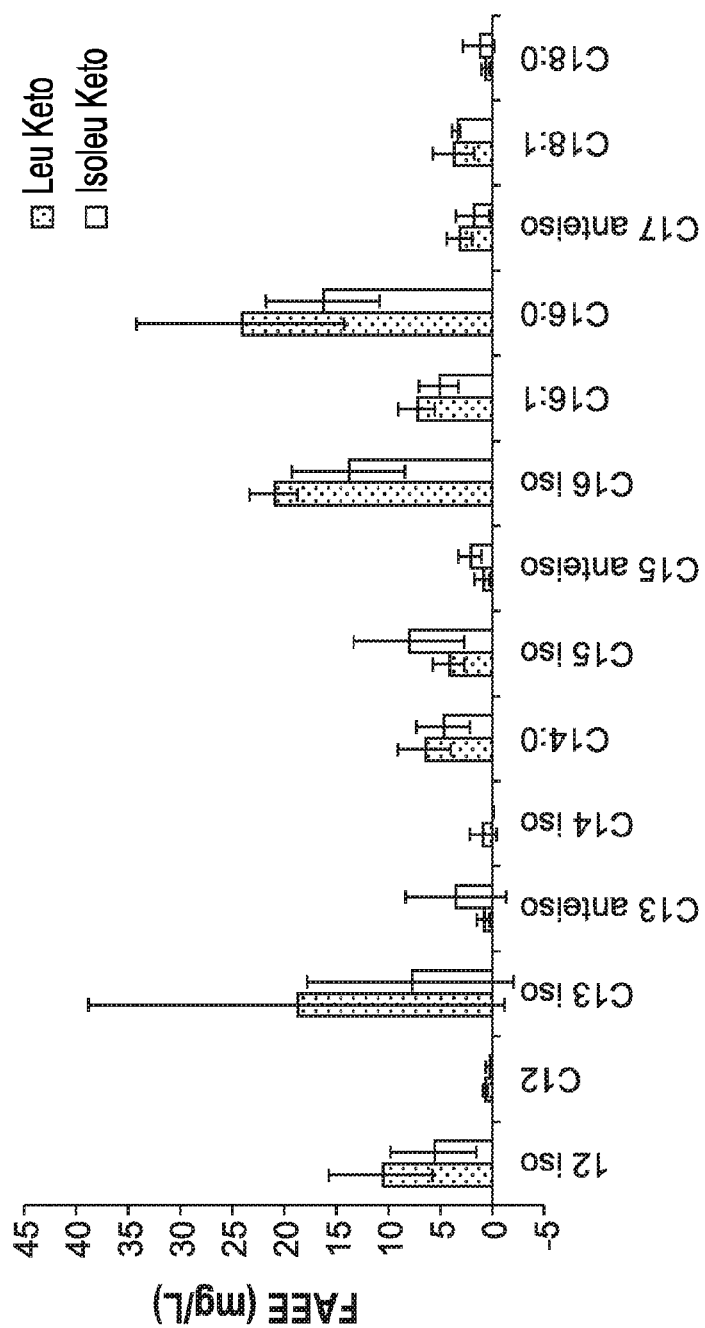
FIG. 11 depicts the production of branched-chain fatty acid ethyl esters (FAEE). The titer for each species of FAEE is reported. Total FAEE averaged 70 mg/L, with 39 mg/L comprising branched-chain FAEE, or 54% of total FAEE.

FadD can accept a branched-chain fatty acid substrate. FAEE can be formed through the activation of a free fatty acid to acyl-CoA followed by a transesterification with ethanol. In this case, a wax-ester synthase (encoded by atfA) along with the acyl-CoA synthase (encoded by fadD) were expressed in conjunction with the branched-chain fatty acid production pathway. The free branched-chain fatty acid generated via the BCFA pathway can be activated to a fatty acyl-CoA by FadD, then trans-esterified with ethanol, either produced endogenously or supplemented exogenously, to form a branched-chain fatty acid ethyl ester. The engineered branched-chain fatty acid ethyl ester pathway produced 70 mg/L total FAEE and 39 mg/L BCFAEE, reaching 54% of total FAEE (FIG. 11). Further optimizations are expected to increase the titer further.

Example 9

In this Example, an endogenous pathway for enhanced lipoylation without lipoic acid supplementation was engineered.

Figure 12A:
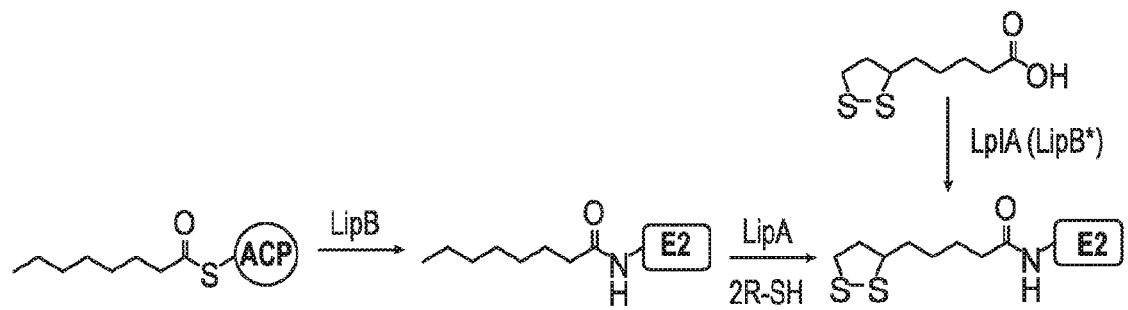
FIGS. 12A & 12B depict the engineering of the endogenous lipoylation pathway for BCFA production.
Figure 12B:
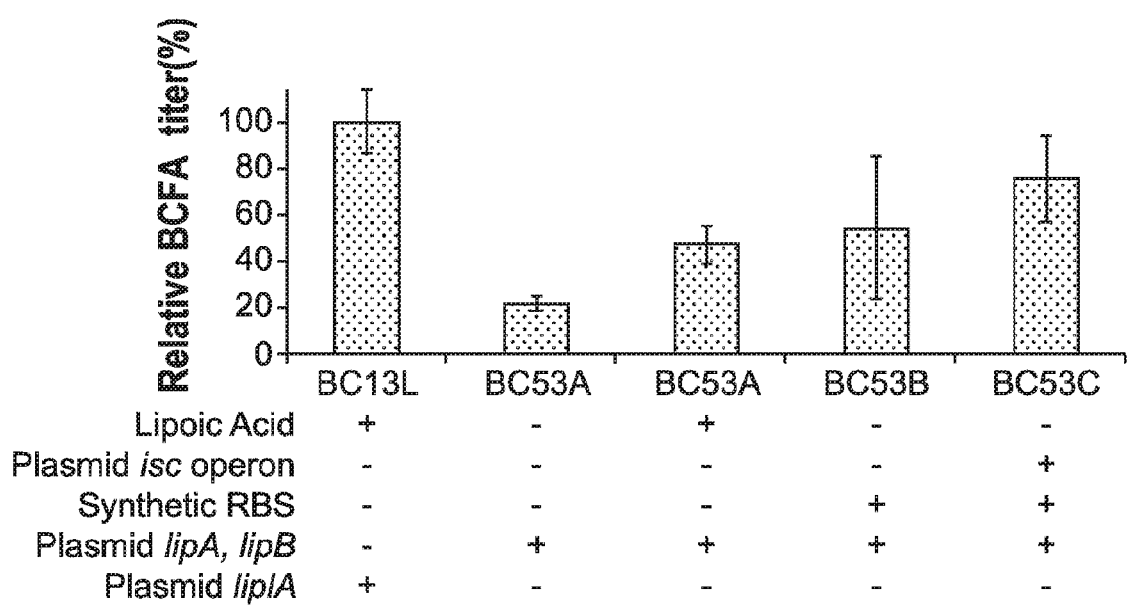

The basic endogenous lipoylation pathway contains a lipoyl(octanoyl) transferase (encoded by lipB) and a lipoyl synthase (encoded by lipA) (see, FIG. 12A). When lipA and lipB were coexpressed under the control of a $P_{BAD}$ promoter with native ribosome binding sites (RBSs), BCFA production reached 22% of that produced with the strain engineered with the exogenous lipoylation pathway with lipoic acid supplementation (FIG. 12B). Placing LipA and LipB under the control of strong, synthetic RBSs increased BCFA production by 32%, yet only reached 54% of that produced by the strain with added lipoic acid. To increase LipA function, the LipA-LipB pathway was coexpressed with seven iron-sulfur-cluster chaperones (isc operon, encoded by iscS, iscU, iscA, hscB, hscA, fdx, iscX), which improved BCFA production to 75% of that achieved by the strain containing the exogenous lipoylation pathway (see, FIG. 12B). All strains were cultivated in parallel and supplemented with 1 g/L 4-methyl-2-oxopentanoic acid.

Disclosed herein are transformed host cells and methods for producing branched-chain acyl-ACPs. Also disclosed herein are transformed host cells and methods for producing branched chain fatty acids in high proportion and in high titer. Also disclosed are methods for producing specific branched-chain fatty acid species. Production of 80% BCFA represents a significant advance in the field as previous methods resulted in both low titers and low percentage. With functionalized BKD, the transformed host cells and methods provided herein allow for the reliable production of greater than 79% BCFA, and of that percentage of BCFA, individual species produced can be tightly controlled by supply of the α-keto acid precursor at an average of 50% of total fatty acids. This platform can be applied for branched-chain alkane production, branched-chain fatty alcohols, or branched-chain fatty acid ethyl esters, all of which have valuable fuel properties.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A transformed host cell for producing a branched-chain acyl-acyl carrier protein (acyl-ACP) comprising: a nucleic acid encoding a branched-chain α-keto acid dehydrogenase; a nucleic acid encoding a branched-chain-specific β-ketoacyl-[acyl-carrier-protein] synthase III; and a nucleic acid encoding a lipoyl ligase A; wherein at least one of the nucleic acids is operably linked to a nucleic acid encoding an iron sulfur cluster chaperone.

2. A method for producing a branched-chain acyl-acyl carrier protein (acyl-ACP), the method comprising:
providing a transformed host cell comprising a nucleic acid encoding a branched-chain α-keto acid dehydrogenase; a nucleic acid encoding a β-ketoacyl-[acyl-carrier-protein] synthase III; a nucleic acid encoding a lipoyl ligase A; and wherein at least one of the nucleic acids is operably linked to a nucleic acid encoding an iron sulfur cluster chaperone; and culturing the transformed host cell in a culture medium comprising lipoic acid under conditions permitting the transformed host cell to produce a branched-chain acyl-ACP.

3. A method for producing specific branched-chain fatty acid species, the method comprising:
providing a transformed host cell comprising a nucleic acid comprising a sequence encoding a branched-chain α-keto acid dehydrogenase; a nucleic acid comprising a sequence encoding a branched-chain-specific β-ketoa- cyl-[acyl-carrier-protein]synthase III; and a nucleic acid encoding a lipoyl ligase A; and wherein the branched-chain-specific β-Ketoacyl-(acyl-carrier-protein) synthase III is selected from the group consisting of Staphylococcus aureus FabH (saFabH); Bacillus subtilis FabH2 ($_{Bs}$FabH2); Bacillus subtilis FabH ($_{Bs}$FabHI); and a Listeria monocytogenes FabH; and wherein at least one of the nucleic acids is operably linked to a nucleic acid encoding an iron sulfur cluster chaperone;
culturing the transformed host cell in a culture medium comprising lipoic acid and an α-keto acid, wherein the transformed host cell produces a specific branched-chain fatty acid species.

4. The host cell of claim 1 wherein the nucleic acid encoding a branched-chain α-keto acid dehydrogenase has about 95% sequence identity to a sequence selected from the group consisting of SEQ ID NO:1, SEQ ID NO:2, SEQ ID NO:3 and SEQ ID NO:4.

5. The host cell of claim 1 wherein the nucleic acid encoding a lipoyl ligase A has about 95% sequence identity to SEQ ID NO:9.

6. The host cell of claim 1 wherein the branched-chain-specific β-Ketoacyl-(acyl-carrier-protein) synthase III is selected from the group consisting of $_{Sa}$FabH; $_{Bs}$FabH2; $_{Bs}$FabH1; and a Listeria monocytogenes FabH.

7. The host cell of claim 1 further comprising a nucleic acid encoding a FadR.

8. The host cell of claim 1 wherein the host cell is selected from the group consisting of *Escherichia, Saccharomyces* sp., and cyanobacteria.

9. The method of claim 3 wherein the branched-chain fatty acid is produced at a percentage of greater than 79% of the total fatty acids produced.

10. The method of claim 3 wherein the branched-chain fatty acid produced is increased by about 4-fold as compared to a host cell cultured in a culture medium lacking lipoic acid.

11. The method of claim 3 wherein the branched-chain fatty acid produced comprises one of an odd-chain-iso branched-chain fatty acid; an even-chain-iso branched-chain fatty acid; an odd-chain ante-iso branched-chain fatty acid; and combinations thereof.

12. The method of claim 11 wherein the odd-chain-iso branched-chain fatty acid is selected from 7-methyl-octanoic acid (C9 iso), 9-methyl-decanoic acid (C11 iso), 11-methyl-dodecanoic aid (C13 iso), 13-methyl-tetradecanoic acid (C15 iso), 15-methyl-hexadecanoic acid (C17 iso) and combinations thereof; wherein the even-chain-iso branched-chain fatty acid is selected from 10-methyl-undecanoic acid (C12 iso), 12-methyl-tridecanoic acid (C14 iso), 14-methyl-pentadecanoic acid (C16 iso), 16-methyl-heptadecanoic acid (C18 iso) and combinations thereof; and wherein the odd-chain ante-iso branched-chain fatty acid is selected from 6-methyl-octanoic acid (C9 anteiso), 8-methyl-decanoic acid (C11 anteiso), 10-methyl-dodeanoic acid (C13 anteiso), 12-methyl-tetradecanoic acid (C15 anteiso), 14-methyl-hexadecanoic acid (C17 anteiso), and combinations thereof.

13. The method of claim 3 wherein the nucleic acid encoding a branched-chain α-keto acid dehydrogenase has about 95% sequence identity to a sequence selected from the group consisting of SEQ ID NO:1, SEQ ID NO:2, SEQ ID NO:3 and SEQ ID NO:4.

14. The method of claim 3 wherein the nucleic acid encoding a lipoyl ligase A has about 95% sequence identity to SEQ ID NO:9.

15. The host cell of claim 3 wherein the host cell further comprises a nucleic acid encoding a FadR.

16. The method of claim 3 wherein the host cell is selected from the group consisting of *Escherichia, Saccharomyces* sp., and cyanobacteria.

17. The method of claim 13 wherein the culture medium further comprises an α-keto acid.

18. The method of claim 17 wherein the α-keto acid is selected from the group consisting of 3-methyl-2-oxobutyric acid, 4-methyl-2-oxopentanoic acid and 3-methyl-2-oxopentanoic acid.

* * * * *

SEQUENCE LISTING

```
<160> NUMBER OF SEQ ID NOS: 11

<210> SEQ ID NO 1
<211> LENGTH: 993
<212> TYPE: DNA
<213> ORGANISM: Bacillus subtilis

<400> SEQUENCE: 1
atgagtacaa accgacatca agcactaggg ctgactgatc aggaagccgt tgatatgtat        60
```

-continued

| | |
|---|---|
| agaaccatgc tgttagcaag aaaaatcgat gaaagaatgt ggctgttaaa ccgttctggc | 120 |
| aaaattccat ttgtaatctc ttgtcaagga caggaagcag cacaggtagg agcggctttc | 180 |
| gcacttgacc gtgaaatgga ttatgtattg ccgtactaca gagacatggg tgtcgtgctc | 240 |
| gcgtttggca tgacagcaaa ggacttaatg atgtccgggt ttgcaaaagc agcagatccg | 300 |
| aactcaggag gccgccagat gccgggacat tccgacaaa agaaaaaccg cattgtgacg | 360 |
| ggatcatctc cggttacaac gcaagtgccg cacgcagtcg gtattgcgct tgcgggacgt | 420 |
| atggagaaaa aggatatcgc agcctttgtt acattcgggg aagggtcttc aaaccaaggc | 480 |
| gatttccatg aaggggcaaa ctttgccgct gtccataagc tgccggttat tttcatgtgt | 540 |
| gaaaacaaca atacgcaat ctcagtgcct tacgataagc aagtcgcatg tgagaacatt | 600 |
| tccgaccgtg ccataggcta tgggatgcct ggcgtaactg tgaatggaaa tgatccgctg | 660 |
| gaagtttatc aagcggttaa agaagcacgc gaaagggcac gcagaggaga aggcccgaca | 720 |
| ttaattgaaa cgatttctta ccgccttaca ccacattcca gtgatgacga tgacagcagc | 780 |
| tacagaggcc gtgaagaagt agaggaagcg aaaaaaagtg atcccctgct tacttatcaa | 840 |
| gcttacttaa aggaaacagg cctgctgtcc gatgagatag aacaaaccat gctggatgaa | 900 |
| attatggcaa tcgtaaatga agcgacggat gaagcggaga acgccccata tgcagctcct | 960 |
| gagtcagcgc ttgattatgt ttatgcgaag tag | 993 |

<210> SEQ ID NO 2
<211> LENGTH: 984
<212> TYPE: DNA
<213> ORGANISM: Bacillus subtilis

<400> SEQUENCE: 2

| | |
|---|---|
| atgtcagtaa tgtcatatat tgatgcaatc aatttggcga tgaaagaaga aatggaacga | 60 |
| gattctcgcg ttttcgtcct tggggaagat gtaggaagaa aaggcggtgt gtttaaagcg | 120 |
| acagcgggac tctatgaaca atttggggaa gagcgcgtta tggatacgcc gcttgctgaa | 180 |
| tctgcaatcg caggagtcgg tatcggagcg gcaatgtacg gaatgagacc gattgctgaa | 240 |
| atgcagtttg ctgatttcat tatgccggca gtcaaccaaa ttatttctga agcggctaaa | 300 |
| atccgctacc gcagcaacaa tgactggagc tgtccgattg tcgtcagagc gccatacggc | 360 |
| ggaggcgtgc acggagccct gtatcattct caatcagtcg aagcaatttt cgccaaccag | 420 |
| cccggactga aaattgtcat gccatcaaca ccatatgacg cgaaagggct cttaaaagcc | 480 |
| gcagttcgtg acgaagaccc cgtgctgttt tttgagcaca gcgggcata ccgtctgata | 540 |
| aagggcgagg ttccggctga tgattatgtc ctgccaatcg gcaaggcgga cgtaaaaagg | 600 |
| gaaggcgacg acatcacagt gatcacatac ggcctgtgtg tccacttcgc cttacaagct | 660 |
| gcagaacgtc tcgaaaaaga tggcatttca gcgcatgtgg tggatttaag aacagtttac | 720 |
| ccgcttgata aagaagccat catcgaagct gcgtccaaaa ctggaaaggt tcttttggtc | 780 |
| acagaagata caaaagaagg cagcatcatg agcgaagtag ccgcaattat atccgagcat | 840 |
| tgtctgttcg acttagacgc gccgatcaaa cggcttgcag gtcctgatat tccggctatg | 900 |
| ccttatgcgc cgacaatgga aaaatacttt atggtcaacc ctgataaagt ggaagcggcg | 960 |
| atgagagaat tagcggagtt ttaa | 984 |

<210> SEQ ID NO 3
<211> LENGTH: 1275
<212> TYPE: DNA
<213> ORGANISM: Bacillus subtilis

<400> SEQUENCE: 3

```
atggcaattg aacaaatgac gatgccgcag cttggagaaa gcgtaacaga ggggacgatc      60
agcaaatggc ttgtcgcccc cggtgataaa gtgaacaaat acgatccgat cgcggaagtc     120
atgacagata aggtaaatgc agaggttccg tcttctttta ctggtacgat aacagagctt     180
gtgggagaag aaggccaaac cctgcaagtc ggagaaatga tttgcaaaat tgaaacagaa     240
ggcgcgaatc cggctgaaca aaacaagaa cagccagcag catcagaagc cgctgagaac      300
cctgttgcaa aaagtgctgg agcagccgat cagcccaata aaagcgcta ctcgccagct       360
gttctccgtt tggccggaga gcacggcatt gacctcgatc aagtgacagg aactggtgcc     420
ggcgggcgca tcacacgaaa agatattcag cgcttaattg aaacaggcgg cgtgcaagaa     480
cagaatcctg aggagctgaa acagcagct cctgcaccga gtctgcatc aaacctgag        540
ccaaaagaag agacgtcata tcctgcgtct gcagccggtg ataaagaaat ccctgtcaca     600
ggtgtaagaa aagcaattgc ttccaatatg aagcgaagca aaacagaaat tccgcatgct     660
tggacgatga tggaagtcga cgtcacaaat atggttgcat atcgcaacag tataaaagat     720
tcttttaaga agacagaagg ctttaattta acgttcttcg cctttttttgt aaaagcggtc    780
gctcaggcgt taaaagaatt cccgcaaatg aatagcatgt gggcggggga caaaattatt     840
cagaaaaagg atatcaatat ttcaattgca gttgccacag aggattcttt atttgttccg     900
gtgattaaaa acgctgatga aaaacaatt aaaggcattg cgaaagacat taccggccta      960
gctaaaaaag taagagacgg aaaactcact gcagatgaca tgcagggagg cacgtttacc    1020
gtcaacaaca caggttcgtt cgggtctgtt cagtcgatgg cattatcaa ctaccctcag     1080
gctgcgattc ttcaagtaga atccatcgtc aaacgcccgg ttgtcatgga caatggcatg    1140
attgctgtca gagacatggt taatctgtgc ctgtcattag atcacagagt gcttgacggt    1200
ctcgtgtgcg gacgattcct cggacgagtg aaacaaattt tagaatcgat tgacgagaag    1260
acatctgttt actaa                                                     1275
```

<210> SEQ ID NO 4
<211> LENGTH: 1425
<212> TYPE: DNA
<213> ORGANISM: Bacillus subtilis

<400> SEQUENCE: 4

```
atggcaactg agtatgacgt agtcattctg ggcggcggta ccggcggtta tgttgcggcc       60
atcagagccg ctcagctcgg cttaaaaaca gccgttgtgg aaaaggaaaa actcggggga     120
acatgtctgc ataaaggctg tatcccgagt aaagcgctgc ttagaagcgc agaggtatac     180
cggacagctc gtgaagccga tcaattcgga gtggaaacgg ctggcgtgtc cctcaacttt     240
gaaaaagtgc agcagcgtaa gcaagccgtt gttgataagc ttgcagcggg tgtaaatcat     300
ttaatgaaaa aggaaaaat tgacgtgtac accggatatg acgtatcct ggaccgtca       360
atcttctctc cgctgccggg aacaatttct gttgagcggg aaatggcga agaaaatgac      420
atgctgatcc cgaaacaagt gatcattgca acaggatcaa gaccgagaat gcttccgggt    480
cttgaagtgg acggtaagtc tgtactgact tcagatgagg cgctccaaat ggaggagctg    540
ccacagtcaa tcatcattgt cggcggaggg ttatcggta tcgaatgggc gtctatgctt      600
catgattttg gcgttaaggt aacggttatt gaatacgcgg atcgcatatt gccgactgaa    660
gatctagaga tttcaaaaga aatggaaagt cttcttaaga aaaaaggcat ccagttcata    720
```

| | |
|---|---|
| acaggggcaa aagtgctgcc tgacacaatg acaaaaacat cagacgatat cagcatacaa | 780 |
| gcggaaaaag acggagaaac cgttacctat tctgctgaga aaatgcttgt ttccatcggc | 840 |
| agacaggcaa atatcgaagg catcggccta gagaacaccg atattgttac tgaaaatggc | 900 |
| atgatttcag tcaatgaaag ctgccaaacg aaggaatctc atatttatgc aatcggagac | 960 |
| gtaatcggtg gcctgcagtt agctcacgtt gcttcacatg agggaattat tgctgttgag | 1020 |
| cattttgcag gtctcaatcc gcatccgctt gatccgacgc ttgtgccgaa gtgcatttac | 1080 |
| tcaagccctg aagctgccag tgtcggctta accgaagacg aagcaaaggc gaacgggcat | 1140 |
| aatgtcaaaa tcggcaagtt cccatttatg gcgattggaa aagcgcttgt atacggtgaa | 1200 |
| agcgacggtt ttgtcaaaat cgtggctgac cgagatacag atgatattct cggcgttcat | 1260 |
| atgattggcc gcatgtcac cgacatgatt tctgaagcgg tcttgccaa agtgctggac | 1320 |
| gcaacaccgt gggaggtcgg gcaaacgatt caccccgcatc aacgctttc tgaagcaatt | 1380 |
| ggagaagctg cgcttgccgc agatggcaaa gccattcatt tttaa | 1425 |

<210> SEQ ID NO 5
<211> LENGTH: 942
<212> TYPE: DNA
<213> ORGANISM: Staphylococcus aureus

<400> SEQUENCE: 5

| | |
|---|---|
| atgaacgtgg gtattaaagg ttttggtgca tatgcgccag aaaagattat tgacaatgcc | 60 |
| tattttgagc aattttttaga tacatctgat gaatggattt ctaagatgac tggaattaaa | 120 |
| gaaagacatt gggcagatga tgatcaagat acttcagatt tagcatatga agcaagttta | 180 |
| aaagcaatcg ctgacgctgg tattcagccc gaagatatag atatgataat tgttgccaca | 240 |
| gcaactggag atatgccatt tccaactgtc gcaaatatgt tgcaagaacg tttagggacg | 300 |
| ggcaaagttg cctctatgga tcaacttgca gcatgttctg gatttatgta ttcaatgatt | 360 |
| acagctaaac aatatgttca atctggagat tatcataaca ttttagttgt cggtgcagat | 420 |
| aaattatcta aaataacaga tttaactgac cgttctactg cagttctatt tggagatggt | 480 |
| gcaggtgcgg ttatcatcgg tgaagtttca gatggcagag gtattataag ttatgaaatg | 540 |
| ggttctgatg gcacaggtgg taaacattta tatttagata agatactgg taaactgaaa | 600 |
| atgaatggtc gagaagtatt taaatttgct gttagaatta tgggtgatgc atcaacacgt | 660 |
| gtagttgaaa aagcgaattt aacatcagat gatatagatt tatttattcc tcatcaagct | 720 |
| aatattgaaa ttatggaatc agctagagaa cgcttaggta tttcaaaaga caaaatgagt | 780 |
| gtttctgtaa ataaatatgg aaatacttca gctgcgtcaa tacctttaag tatcgatcaa | 840 |
| gaattaaaaa atggtaaaat caaagatgat gatacaattg ttcttgtcgg attcggtggc | 900 |
| ggcctaactt ggggcgcaat gacaataaaa tggggaaaat ag | 942 |

<210> SEQ ID NO 6
<211> LENGTH: 978
<212> TYPE: DNA
<213> ORGANISM: Bacillus subtilis

<400> SEQUENCE: 6

| | |
|---|---|
| atgtcaaaag caaaaattac agctatcggc acctatgcgc cgagcagacg tttaaccaat | 60 |
| gcagatttag aaaagatcgt tgatacctct gatgaatgga tcgttcagcg cacaggaatg | 120 |
| agagaacgcc ggattgcgga tgaacatcaa tttacctctg attatgcat agaagcggtg | 180 |
| aagaatctca gagccgttta taaggaacg cttgatgatg tcgatatgat cctcgttgcc | 240 |

```
acaaccacat ccgattacgc ctttccgagt acggcatgcc gcgtacagga atatttcggc    300
tgggaaagca ccggcgcgct ggatattaat gcgacatgcg ccgggctgac atacggcctc    360
catttggcaa atggattgat cacatctggc cttcatcaaa aaattctcgt catcgccgga    420
gagacgttat caaaggtaac cgattatacc gatcgaacga catgcgtact gttcggcgat    480
gccgcgggtg cgctgttagt agaacgagat gaagagacgc cgggatttct tgcgtctgta    540
caaggaacaa gcgggaacgg cggcgatatt ttgtatcgtg ccggactgcg aaatgaaata    600
aacggtgtgc agcttgtcgg ttccggaaaa atggtgcaaa acggacgcga ggtatataaa    660
tgggccgcaa gaaccgtccc tggcgaattt gaacggcttt tacataaagc aggactcagc    720
tccgatgatc tcgattggtt tgttcctcac agcgccaact tgcgcatgat cgagtcaatt    780
tgtgaaaaaa caccgttccc gattgaaaaa acgctcacta gtgttgagca ctacggaaac    840
acgtcttcgg tttcaattgt tttggcgctc gatctcgcag tgaaagccgg gaagctgaaa    900
aaagatcaaa tcgttttgct tttcgggttt ggcggcggat taacctatac aggattgctt    960
attaaatggg ggatgtaa                                                  978

<210> SEQ ID NO 7
<211> LENGTH: 552
<212> TYPE: DNA
<213> ORGANISM: Artificial Sequence
<220> FEATURE:
<223> OTHER INFORMATION: Synthetic

<400> SEQUENCE: 7
atggcggaca cgttattgat tctgggtgat agcctgagcg ccgggtatcg aatgtctgcc     60
agcgcggcct ggcctgcctt gttgaatgat aagtggcaga gtaaaacgtc ggtagttaat    120
gccagcatca gcggcgacac ctcgcaacaa ggactggcgc gccttccggc tctgctgaaa    180
cagcatcagc cgcgttgggt gctggttgaa ctgggcggca tgacggtttt cgtggttttt    240
cagccacagc aaaccgagca aacgctgcgc cagattttgc aggatgtcaa agccgccaac    300
gctgaaccat tgttaatgca atacgtctg cctgcaaact atggtcgccg ttataatgaa    360
gcctttagcg ccatttaccc caaactcgcc aaagagtttg atgttccgct gctgcccttt    420
tttatggaag aggtctacct caagccacaa tggatgcagg atgacggtat tcatcccaac    480
cgcgacgccc agccgtttat tgccgactgg atggcgaagc agttgcagcc tttagtaaat    540
catgactcat aa                                                        552

<210> SEQ ID NO 8
<211> LENGTH: 1017
<212> TYPE: DNA
<213> ORGANISM: Escherichia coli

<400> SEQUENCE: 8
atgtccacat tacgcctgct catctctgac tcttacgacc cgtggtttaa cctggcggtg     60
gaagagtgta tttttcgcca aatgcccgcc acgcagcgcg ttctgtttct ctggcgcaat    120
gccgacacgg tagtaattgg tcgcgcgcag aaccgtggaa agagtgtaa tacccggcgg    180 atggaagaag ataacgtccg cctggcgcgg cgcagtagcg gtggcggcgc ggtgttccac    240
gatctcggca ataccctgct taccttatg gctggcaagc cggagtacga taaaactatc    300
tccacgtcga ttgtgctcaa tgcgctgaac gcgctcggcg tcagcgccga agcgtccgga    360
cgtaacgatc tggtggtgaa aaccgtcgaa ggcgaccgca aagtctcagg ctcggcctat    420
```

```
cgcgaaacca aagatcgcgg cttccaccac ggcaccttgc tactcaatgc cgacctcagc    480
cgcctggcaa actatctcaa tccggataaa aagaaactgg cggcgaaagg cattacgtcg    540
gtacgttccc gcgtgaccaa cctcaccgag ctgttgccgg ggatcaccca tgagcaggtt    600
tgcgaggcca taaccgaggc cttttttcgcc cattatggcg agcgcgtgga agcggaaatc    660
atctccccga acaaaacgcc agacttgcca aacttcgccg aaacctttgc ccgccagagt    720
agctgggaat ggaacttcgg tcaggctccg gcattctcgc atctgctgga tgaacgcttt    780
acctggggcg gcgtggaact gcatttcgac gttgaaaaag gccatatcac ccgcgcccag    840
gtgtttaccg acagcctcaa ccccgcgccg ctggaagccc tcgccggacg actgcaaggc    900
tgcctgtacc gcgcagatat gctgcaacag gagtgcgaag cgctgttggt tgacttcccg    960
gaacaggaaa aagagctacg ggagttatcg gcatggatgg cggggctgt aaggtag     1017
```

```
<210> SEQ ID NO 9
<211> LENGTH: 720
<212> TYPE: DNA
<213> ORGANISM: Escherichia coli

<400> SEQUENCE: 9
atggtcatta aggcgcaaag cccggcgggt ttcgcggaag agtacattat tgaaagtatc     60
tggaataacc gcttccctcc cgggactatt tgcccgcag aacgtgaact ttcagaatta    120
attggcgtaa cgcgtactac gttacgtgaa gtgttacagc gtctggcacg agatggctgg    180
ttgaccattc aacatggcaa gccgacgaag gtgaataatt tctgggaaac ttccggttta    240
aatatccttg aaacactggc gcgactggat cacgaaagtg tgccgcagct tattgataat    300
ttgctgtcgg tgcgtaccaa tatttccact attttttattc gcaccgcgtt tcgtcagcat    360
cccgataaag cgcaggaagt gctggctacc gctaatgaag tggccgatca cgccgatgcc    420
tttgccgagc tggattacaa catattccgc ggcctggcgt ttgcttccgg caacccgatt    480
tacggtctga ttcttaacgg gatgaaaggg ctgtatacgc gtattggtcg tcactatttc    540
gccaatccgg aagcgcgcag tctggcgctg gcttctacc acaaactgtc ggcgttgtgc    600
agtgaaggcg cgcacgatca ggtgtacgaa acagtgcgtc gctatgggca tgagagtggc    660
gagatttggc accggatgca gaaaaatctg ccgggtgatt tagccattca ggggcgataa    720
```

```
<210> SEQ ID NO 10
<211> LENGTH: 642
<212> TYPE: DNA
<213> ORGANISM: Escherichia coli

<400> SEQUENCE: 10
ttgtatcagg ataaaattct tgtccgccag ctcggtcttc agccttacga gccaatctcc     60
caggctatgc atgaattcac cgatacccgc gatgatagta cccttgatga atctggctg    120 gtcgagcact atccggtatt cacccaaggt caggcaggaa aagcggagca ttttaatg    180 ccgggtgata ttccggtgat ccagagcgat cgcgtgggc aggtgactta tcacgggccg    240
gggcaacagg tgatgtatgt gttgcttaac ctgaaacgcc gtaaactcgg tgtgcgtgaa    300 ctggtgaccct tgcttgagca acagtggtg aatacccctgg ctgaactggg tatagaagcg    360
catcctcggg ctgacgcgcc aggtgtctat gttggggaaa agaaatttg ctcactgggt    420 ttacgtattc gacgcggttg ttcattccac ggtctggcat taaacgtcaa tatggatctt    480
tcaccatttt tacgtattaa tccttgtggg tatgccggaa tggaaatggc taaaatatca    540
caatggaaac ccgaagcgac gactaataat attgctccac gtttactgga aatatttta    600
```

```
gcgctactaa acaatccgga cttcgaatat attaccgctt aa                642
```

<210> SEQ ID NO 11
<211> LENGTH: 966
<212> TYPE: DNA
<213> ORGANISM: Escherichia coli

<400> SEQUENCE: 11

```
atgagtaaac ccattgtgat ggaacgcggt gttaaatacc gcgatgccga taagatggcc    60
cttatcccgg ttaaaaacgt ggcaacagag cgcgaagccc tgctgcgcaa gccggaatgg   120
atgaaaatca agcttccagc ggactctaca cgtatccagg gcatcaaagc cgcaatgcgc   180
aaaaatggcc tgcattctgt ctgcgaggaa gcctcctgcc ctaacctggc ggaatgcttc   240
aaccacggca cagcaacgtt tatgatcctc ggcgctattt gtacccgccg ttgtccgttc   300
tgtgatgttg cccacggtcg cccggtagct cctgatgcca atgaaccagt gaaactggcg   360
cagaccattg ccgatatggc gctgcgttat gtggttatca cctccgttga ccgtgatgac   420
ctgcgcgatg gcggtgccca gcactttgcg gattgcatta ctgccattcg ggaaaaaagc   480
ccgcaaatca aaattgaaac tctggtgccg gatttccgcg tcgtatgga tcgtgctctg   540 gatattctga ctgcaacgcc accagatgtg ttcaaccata acctggaaaa cgtaccgcgt   600
atttaccgtc aggtacggcc tggtgcagat tacaactggt cgctgaagct gctggaacgc   660
tttaaagaag cgcatccgga aatcccgacc aagtctggtc tgatggtggg actgggtgaa   720
accaatgaag aaattattga ggtaatgcgc gacctgcgcc gtcatggtgt gacgatgtta   780
acgctggggc aatatttgca gccaagccgc catcacctgc cggttcaacg ttacgttagc   840
ccggatgagt cgacgaaat gaaagccgaa gcgctggcga tgggctttac ccatgctgca   900
tgcggtccgt ttgtccgctc ttcttaccac gccgatttgc aggcgaaagg gatggaagtt   960
aagtaa                                                              966
```